US006463317B1

(12) United States Patent
Kucharczyk et al.

(10) Patent No.: US 6,463,317 B1
(45) Date of Patent: Oct. 8, 2002

(54) DEVICE AND METHOD FOR THE ENDOVASCULAR TREATMENT OF ANEURYSMS

(75) Inventors: John Kucharczyk, Minneapolis, MN (US); Richard Latchaw, Miami, FL (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/081,319

(22) Filed: May 19, 1998

(51) Int. Cl.[7] .............................. A61B 5/055; A61B 5/00
(52) U.S. Cl. ...................... 600/411; 600/420; 600/424; 600/427; 600/435; 606/194; 606/195
(58) Field of Search .................................. 600/411, 420, 600/423, 424, 427, 431, 433–435; 604/27, 28, 507–510, 93.01, 94.01, 96.01, 97.01, 101.04, 103.1, 103.13, 103.14; 606/191–192, 194, 195, 198

(56) References Cited

U.S. PATENT DOCUMENTS

| 3,055,370 A | 9/1962 | McKinney et al. |
| 3,554,186 A | 1/1971 | Leksell et al. |

(List continued on next page.)

FOREIGN PATENT DOCUMENTS

| DE | 19648246 | 5/1998 | ............ A61L/29/00 |
| EP | 0352325 | 1/1990 | ............ A61M/25/00 |
| EP | 0442329 | 8/1991 | ............. G01D/5/18 |
| EP | 0826342 | 3/1998 | ............ A61B/17/12 |
| WO | 93/05706 | 4/1993 | ............ A61B/5/055 |
| WO | 93/15784 | 8/1993 | ............ A61M/25/00 |
| WO | 93/15785 | 8/1993 | ............ A61M/25/00 |
| WO | 93/15872 | 8/1993 | ............. B23P/17/00 |
| WO | 94/27697 | 12/1994 | ............ A65M/25/00 |
| WO | 96/33761 | 10/1996 | ............ A61M/25/00 |
| WO | 97/27893 | 8/1997 | ............ A61M/19/00 |
| WO | 98/26832 | 6/1998 | ............ A61M/31/00 |

OTHER PUBLICATIONS

Basser, P.J., "Interstitial Pressure, Volume, and Flow during Infusion into Brain Tissue", *Microvascular Research* 44 (2), 143–165, (Sep. 1992).

(List continued on next page.)

*Primary Examiner*—Ruth S. Smith
(74) *Attorney, Agent, or Firm*—Mark A. Litman & Assoc., P.A.

(57) ABSTRACT

This invention provides a method and a device for treating hemodynamically significant aneurysms especially in the intracranial and extracranial circulation regions using either X-ray fluoroscopy or real-time magnetic resonance (MR) imaging guidance. An MR-visible parachute-shaped occlusion device, e.g., containing multiple elongated filamentary loops made of a memory metal, elastomeric hydrogel or other expansile material, is deployed into the aneurysm by radial expansion of the expansile material outwardly into contact with the interior aneurysm surface. The device is firmly positioned against the interior aneurysm surface using a coating which adheres to that interior aneurysm surface. The device may be filled with a hardenable polymer for permanent and complete aneurysm occlusion. Wide-neck aneurysms may be treated with the same device, with the addition of a temporary balloon expanded in the parent vessel to allow expansion of the occluding device within the aneurysm, instillation of the polymer into the device, and detachment of the device from the transporting catheter. Detachment of the aneurysm occlusion device from a transport catheter is achieved by mechanical, electrical and/or chemical decoupling. A coating applied to the surface of the parachute device may induce thrombotic occlusion of the aneurysm by timed delivery of biologic modifier drugs which promote collagen formation, fibroblast growth, and endothelial ingrowth within the aneurysm. The catheter systems may have attached microcoils or may be impregnated with MR-visible agents to permit visualization in MR imaging systems.

26 Claims, 5 Drawing Sheets

U.S. PATENT DOCUMENTS

| | | | |
|---|---|---|---|
| 3,705,938 A | 12/1972 | Hyman et al. | |
| 3,857,934 A | 12/1974 | Bernstein et al. | |
| 3,868,956 A | 3/1975 | Alfidi et al. | |
| 3,986,703 A | 10/1976 | Brett et al. | 254/173 R |
| 4,023,175 A | 5/1977 | Brown et al. | 343/17 |
| 4,147,161 A | 4/1979 | Ikebe et al. | |
| 4,259,703 A | 3/1981 | Young et al. | 360/113 |
| 4,284,948 A | 8/1981 | Young | 324/309 |
| 4,284,950 A | 8/1981 | Burl et al. | 324/320 |
| 4,300,096 A | 11/1981 | Harrison et al. | 324/309 |
| 4,316,106 A | 2/1982 | Young et al. | 307/481 |
| 4,338,571 A | 7/1982 | Young | 330/84 |
| 4,338,945 A | 7/1982 | Kosugi et al. | |
| 4,339,716 A | 7/1982 | Young et al. | 324/309 |
| 4,355,282 A | 10/1982 | Young et al. | 324/309 |
| 4,361,807 A | 11/1982 | Burl et al. | 324/309 |
| 4,362,993 A | 12/1982 | Young et al. | 324/309 |
| 4,379,262 A | 4/1983 | Young | 324/309 |
| 4,384,255 A | 5/1983 | Young et al. | 324/309 |
| 4,418,316 A | 11/1983 | Young et al. | 324/309 |
| 4,448,195 A | 5/1984 | LeVeen et al. | |
| 4,449,097 A | 5/1984 | Young et al. | 324/309 |
| 4,454,474 A | 6/1984 | Young | 324/309 |
| 4,458,203 A | 7/1984 | Young | 324/309 |
| 4,503,569 A | 3/1985 | Dotter | |
| 4,520,828 A | 6/1985 | Burl et al. | |
| 4,534,358 A | 8/1985 | Young | |
| 4,553,122 A | 11/1985 | Young | 335/296 |
| 4,554,925 A | 11/1985 | Young | |
| 4,558,278 A | 12/1985 | Young | 324/309 |
| 4,563,647 A | 1/1986 | Young et al. | 324/309 |
| 4,564,813 A | 1/1986 | Young | 324/311 |
| 4,572,198 A | 2/1986 | Codrington | |
| 4,587,488 A | 5/1986 | Young | 324/306 |
| 4,604,578 A | 8/1986 | Young | 324/307 |
| 4,607,221 A | 8/1986 | Young | 324/306 |
| 4,608,977 A | 9/1986 | Brown | |
| 4,631,480 A | 12/1986 | Young | 324/309 |
| 4,631,481 A | 12/1986 | Young | 324/320 |
| 4,638,803 A | 1/1987 | Rand | 128/325 |
| 4,642,568 A | 2/1987 | Young | 324/309 |
| 4,644,275 A | 2/1987 | Young | 324/307 |
| 4,646,023 A | 2/1987 | Young | 324/309 |
| 4,683,432 A | 7/1987 | Young | 324/309 |
| 4,703,269 A | 10/1987 | Young | 324/309 |
| 4,710,403 A | 12/1987 | Krause et al. | 427/304 |
| 4,727,873 A | 3/1988 | Mobin-Uddin | |
| 4,733,183 A | 3/1988 | Young | 324/309 |
| 4,760,337 A | 7/1988 | Young | 324/309 |
| 4,767,973 A | 8/1988 | Jacobsen et al. | 318/652 |
| D298,190 S | 10/1988 | Komai et al. | D6/380 |
| 4,775,556 A | 10/1988 | Krause et al. | 427/272 |
| 4,805,615 A | 2/1989 | Carol | |
| 4,807,620 A | 2/1989 | Strul et al. | |
| 4,824,436 A | 4/1989 | Wolinsky | 604/53 |
| 4,827,931 A | 5/1989 | Longmore | |
| 4,864,240 A | 9/1989 | Young | 324/318 |
| 4,869,247 A | 9/1989 | Howard, III et al. | |
| 4,882,560 A | 11/1989 | Young et al. | 335/299 |
| 4,885,448 A | 12/1989 | Kasner et al. | 219/121.69 |
| 4,892,538 A | 1/1990 | Aebischer et al. | 604/891.1 |
| 4,914,608 A | 4/1990 | LeBihan et al. | 364/557 |
| 4,922,924 A | 5/1990 | Gambale et al. | |
| 4,941,874 A | 7/1990 | Sandow et al. | 604/60 |
| 4,951,064 A | 8/1990 | Kun et al. | 346/107 R |
| 4,955,891 A | 9/1990 | Carol | 606/130 |
| 4,973,304 A | 11/1990 | Graham et al. | 604/48 |
| 4,989,608 A | 2/1991 | Ratner | |
| 4,994,069 A | 2/1991 | Ritchart et al. | 606/191 |
| 4,994,071 A | 2/1991 | MacGregor | 606/194 |
| 4,998,539 A | 3/1991 | Delsanti | |
| 4,998,938 A | 3/1991 | Ghajar et al. | 606/130 |
| 5,015,955 A | 5/1991 | Young | 324/309 |
| 5,017,566 A | 5/1991 | Bodor | 514/58 |
| 5,017,824 A | 5/1991 | Phillips et al. | 313/13 |
| 5,018,173 A | 5/1991 | Komai et al. | 378/4 |
| 5,034,691 A | 7/1991 | Young | 324/309 |
| 5,035,231 A | 7/1991 | Kubokawa et al. | |
| 5,035,706 A | 7/1991 | Giantureo et al. | 606/198 |
| 5,036,282 A | 7/1991 | Morich et al. | 324/318 |
| 5,037,427 A | 8/1991 | Harada et al. | 606/108 |
| 5,043,632 A | 8/1991 | Asars et al. | 315/169.3 |
| 5,043,715 A | 8/1991 | Kun et al. | 340/781 |
| 5,057,106 A | 10/1991 | Kasevich et al. | 606/33 |
| 5,087,236 A | 2/1992 | Morimoto | 493/342 |
| 5,087,256 A | 2/1992 | Taylor et al. | 606/28 |
| 5,102,401 A | 4/1992 | Lambert et al. | 604/264 |
| 5,102,402 A | 4/1992 | Dror et al. | 604/265 |
| 5,104,403 A | 4/1992 | Brotzu et al. | 623/1 |
| 5,106,455 A | 4/1992 | Jacobsen et al. | 156/659.1 |
| 5,106,627 A | 4/1992 | Aebischer et al. | 424/424 |
| 5,108,407 A | 4/1992 | Geremia et al. | 606/108 |
| 5,108,420 A | 4/1992 | Marks | 606/213 |
| 5,116,345 A | 5/1992 | Jewell et al. | 606/130 |
| 5,120,322 A | 6/1992 | Davis et al. | 604/265 |
| 5,122,136 A | 6/1992 | Guglielmi et al. | 606/32 |
| 5,125,888 A | 6/1992 | Howard et al. | 600/12 |
| 5,131,392 A | 7/1992 | Jolesz et al. | |
| 5,133,733 A | 7/1992 | Rasmussen et al. | 606/200 |
| 5,138,347 A | 8/1992 | Kun et al. | 346/155 |
| D329,335 S | 9/1992 | Komai et al. | D6/361 |
| D329,338 S | 9/1992 | Komai et al. | D6/370 |
| 5,154,179 A | 10/1992 | Ratner | |
| 5,158,548 A | 10/1992 | Lau et al. | 604/96 |
| 5,167,625 A | 12/1992 | Jacobsen et al. | 604/891.1 |
| 5,171,217 A | 12/1992 | March et al. | 604/53 |
| 5,177,441 A | 1/1993 | Morich et al. | 324/318 |
| D333,042 S | 2/1993 | Komai et al. | D6/370 |
| 5,211,165 A | 5/1993 | Dumoulin et al. | |
| 5,211,166 A | 5/1993 | Sepponen | |
| 5,216,366 A | 6/1993 | Young | 324/307 |
| 5,217,483 A | 6/1993 | Tower | 606/198 |
| 5,221,261 A | 6/1993 | Termin et al. | 604/104 |
| 5,226,902 A | 7/1993 | Bae et al. | 604/892.1 |
| 5,227,726 A | 7/1993 | Young | 324/309 |
| 5,234,456 A | 8/1993 | Silvestrini | 606/194 |
| 5,234,457 A | 8/1993 | Andersen | 606/198 |
| 5,250,071 A | 10/1993 | Palermo | 606/198 |
| 5,258,020 A | 11/1993 | Froix | 623/1 |
| 5,263,963 A | 11/1993 | Garrison et al. | 606/198 |
| 5,269,882 A | 12/1993 | Jacobsen | 156/659.1 |
| 5,270,485 A | 12/1993 | Jacobsen | 174/15.1 |
| 5,271,400 A | 12/1993 | Dumoulin et al. | |
| 5,273,622 A | 12/1993 | Jacobsen | 156/659.1 |
| 5,303,707 A | 4/1994 | Young | |
| 5,304,194 A | 4/1994 | Chee et al. | 606/191 |
| 5,304,197 A | 4/1994 | Pinchuk et al. | 606/194 |
| 5,304,199 A | 4/1994 | Myers | 606/194 |
| 5,307,813 A | 5/1994 | Young | |
| 5,330,500 A | 7/1994 | Song et al. | 606/198 |
| 5,332,625 A | 7/1994 | Dunn et al. | 428/409 |
| 5,334,210 A | 8/1994 | Gianturco | 606/151 |
| 5,342,303 A | 8/1994 | Ghaerzadeh | 604/96 |
| 5,368,566 A | 11/1994 | Crocker | 604/101 |
| 5,370,691 A | 12/1994 | Samson | 623/12 |
| 5,375,596 A | 12/1994 | Twiss et al. | |
| 5,378,239 A | 1/1995 | Termin et al. | 604/104 |
| 5,382,260 A | 1/1995 | Dormandy et al. | 606/151 |
| 5,382,261 A | 1/1995 | Palmaz | 606/158 |

| | | |
|---|---|---|
| 5,382,903 A | 1/1995 | Young .......................... 324/318 |
| 5,383,928 A | 1/1995 | Scott et al. ..................... 623/1 |
| 5,389,195 A | 2/1995 | Ouderkirk et al. ........... 156/643 |
| 5,409,003 A | 4/1995 | Young |
| 5,415,163 A | 5/1995 | Harms et al. |
| 5,443,454 A * | 8/1995 | Tanabe et al. ................ 604/52 |
| 5,447,154 A | 9/1995 | Cinquin et al. |
| 5,451,774 A | 9/1995 | Jacobsen ................ 250/227.24 |
| 5,459,769 A | 10/1995 | Brown ........................... 378/4 |
| 5,470,307 A | 11/1995 | Lindall ......................... 604/20 |
| 5,487,739 A | 1/1996 | Aebischer et al. ......... 604/890.1 |
| 5,514,092 A | 5/1996 | Forman et al. .............. 604/101 |
| 5,528,651 A | 6/1996 | Leksell et al. ................ 378/65 |
| 5,534,779 A | 7/1996 | Young et al. ............... 324/319 |
| 5,569,197 A | 10/1996 | Helmus et al. ............... 604/96 |
| 5,571,089 A | 11/1996 | Crocker ....................... 604/102 |
| 5,573,668 A | 11/1996 | Grosh et al. ................ 210/490 |
| 5,580,575 A | 12/1996 | Unger et al. ................ 424/450 |
| 5,590,654 A | 1/1997 | Prince |
| 5,607,418 A | 3/1997 | Arzbaecher .............. 604/891.1 |
| 5,611,025 A | 3/1997 | Lorensen et al. ........... 395/119 |
| 5,612,728 A | 3/1997 | Kun et al. ................... 347/232 |
| 5,628,730 A | 5/1997 | Shapland et al. ............. 604/21 |
| 5,629,967 A | 5/1997 | Leksell et al. ................ 378/65 |
| 5,646,185 A | 7/1997 | Giaccia et al. .............. 514/548 |
| 5,647,361 A | 7/1997 | Damadian |
| 5,654,864 A | 8/1997 | Ritter et al. ................. 361/141 |
| 5,675,256 A | 10/1997 | Young ......................... 324/320 |
| 5,689,189 A | 11/1997 | Morich et al. .............. 324/318 |
| 5,693,067 A | 12/1997 | Purdy .......................... 606/200 |
| 5,707,335 A | 1/1998 | Howard et al. ............... 600/12 |
| 5,713,358 A | 2/1998 | Mistretta et al. |
| 5,713,359 A | 2/1998 | Dumoulin et al. |
| 5,720,720 A | 2/1998 | Laske et al. .................. 604/49 |
| 5,741,248 A | 4/1998 | Stern et al. .................... 606/21 |
| 5,776,097 A * | 7/1998 | Massoud ..................... 604/101 |
| 5,782,764 A | 7/1998 | Werne ......................... 600/411 |
| 5,795,331 A * | 8/1998 | Cragg et al. ............. 604/96.01 |
| 5,800,392 A | 9/1998 | Racchini ...................... 604/96 |
| 5,800,408 A | 9/1998 | Strauss et al. .............. 604/264 |
| 5,840,701 A | 11/1998 | Hsia ............................ 514/21 |
| 5,861,175 A | 1/1999 | Walters et al. .............. 424/486 |
| 5,868,674 A | 2/1999 | Glowinski et al. .......... 600/410 |
| 6,096,021 A * | 8/2000 | Helm et al. .................. 604/509 |

OTHER PUBLICATIONS

Bouvier, G., et al., "Direct Delivery of Medication into a Brain Tumor through Multiple Chronically Implanted Catheters", *Neurosurgery*, 20 (2), 286–291, (Feb. 1987).

Broaddus, W.C., et al., "Distribution and stability of antisense phosphorothiate oligonucleotides in rodent brain following direct intraparenchymal controlled–rate infusion", *Journal of Neurosurgery*, 88 (4), 734–742, (Apr. 1998).

Cares, H.L., et al., "Laboratory experience with a magnetically guided intravascular catheter system", *Journal of Neurosurgery*, 38 (2), 145–154, (Feb. 1973).

Chandler, W.F., et al., "Use of Implantable Pump Systems for Intraarterial, Intraventricular and Intratumoral Treatment of Malignant Brain Tumors", *Annals of the New York Academy of Sciences*, 531, Neurological Applications of Implanted Drug Pumps, 206–212, (1988).

Driller, J., et al., "A review of medical applications of magnet attraction and detection", *Journal of Medical Engineering & Technology*, 11 (6), 271–277, (Nov./Dec. 1987).

Dubach, M., "Accurate stereotaxic injection by radially curved injection needle", *Neurosurgery*, 29 (1), 144–149, (Jul. 1991).

Gillies, G., et al., "Magnetic Manipulation Instrumentation for Medical Physics Research", *Review of Scientific Instruments*, 65 (3), 533–562, (Mar. 1994).

Grady, M., et al., "Magnetic Stereotaxis: A Technique to Deliver Stereotactic Hyperthermia", *Neurosurgery*, 27 (6), 1010–1016, (Dec. 1990).

Grady, M., et al., "Nonlinear Magnetic Stereotaxis: Three–Dimensional, in vivo Remote Magnetic Manipulation of a Small Object in Canine Brain", *Medical Physics*, 17 (3), AAPM Annual Meeting Issue, St. Louis, MO, 405–415, (May/Jun. 1990).

Grady, M., et al., "Preliminary Experimental Investigation of in vivo Magnetic Manipulation: Results and Potential Application in Hyperthermia", *Medical Physics*, 16 (2), 263–272, (Mar./Apr. 1989).

Hajnal, J.V., et al., "MR Imaging of Anisotropically Restricted Diffusion of Water in the Nervous System: Technical, Anatomic, and Pathologic Considerations", *Journal of Computer Assisted Tomography*, 15 (1), 1–18, (Jan./Feb. 1991).

Hasegawa, Y., et al., "Temperature dependent change of apparent diffusion coefficient of water in normal and ischemic brain of rats", *Journal of Cerebral Blood Flow and Metabolism*, 14 (3), 383–390, (1994).

Hilal, S.K., et al., "Magnetically guided devices for vascular exploration and treatment", *Radiology*, 113 (3), 529–540, (Dec. 1974).

Hilal, S.K., et al., "POD Catheter: A Means for Small Vessel Exploration", *Abstract, Journal of Applied Physics* 40 (3), (Mar. 1, 1969).

Howard, M., et al., "Magnetic Movement of a Brain Thermoceptor", *Neurosurgery*, 24 (3), 444–448, (1989).

Howard, M.A., "Stereotaxic pallidotomy for the treatment of Parkinson's Disease", *Current Surgery*, 54 (1), 31–34, (Jan. 1997).

Howard, M.A., et al., "An integrated multipurpose lesion–making electrode", *Neurosurgery*, 42 (1), 137–142, (Jan. 1998).

Howard, M.A., et al., "Magnetically guided stereotaxis", *Advanced Neurosurgical Navigation*, Chapter 45, 549–556, (1999).

Hurst, G.C., et al., "Intravascular (Catheter) NMR Receiver Probe: Preliminary Design Analysis and Application to Canine Iliofemoral Imaging", *Magnetic Resonance in Medicine* 24 (2), 343–357, (Apr. 1992).

Johnston, J., et al., "Shiley Infusaid Pump Technology", *Annals of the New York Academy of Sciences 531*, Neurological Applications of Implanted Drug Pumps, 57–65, (1988).

Kucharczyk, J., et al., "Differential Effects of Brain Lesions on Thirst Induced by the Administration of Angiotensin–II to the Preoptic Region, Subfornical Organ and Anterior Third Ventricle", *Brain Research*, 108, 327–337, (1976).

Laske, D.W., et al., "Chronic Interstital Infusion of Protein to Primate Brain: Determination of Drug Distribution and Clearance with Single–Photon Emission Computerized Tomography Imaging", *Journal of Neurosurgery* 87 (4), 586–594, (Oct. 1997).

Lieberman, D.M., et al., "Convection–enhanced distribution of large molecules in gray matter during interstitial drug infusion", *Journal of Neurosurg*, 82 (6), 1021–1029, (Jun. 1995).

Lux, H.D., et al., "The equilibration time course of (K+) o in cat cortex", *Experimental Brain Research*, 17 (2), 190–205, (Apr. 30, 1973).

Martin, A.J., et al., "MR Imaging of Blood Vessels with an Intravascular Coil", *Journal of Magnetic Resonance Imaging* 2 (4), 421–429, (Jul./Aug. 1992).

McNeil, R., et al., "Characteristics of an Improved Magnetic–Implant Guidance System", *IEEE Transactions on Biomedical Engineering*, 42 (8), 802–808, (Aug. 1995).

McNeil, R., et al., "Functional Design Features and Initial Performance Characteristics of a Magnetic–Implant Guidance System for Stereotactic Neurosurgery", *IEEE Transactions on Biomedical Engineering*, 42 (8), 793–801, (Aug. 1995).

Meeker, D., et al., "Optimal Realization of Arbitrary Forces in a Magnetic Stereotaxis System", *IEEE Transactions on Magnetics*, 32 (2), 320–328, (Mar. 1996).

Molcho, J., et al., "Selective cerebral catheterization", *IEEE Transsctions on Biomedical Engineering*, 17 (2), 134–140, (Apr. 1970).

Molloy, J., et al., "Experimental Determination of the Force Required for Insertion of a Thermoseed into Deep Brain Tissues", *Annals of Biomedical Engineering*, 18, 299–313, (1990).

Molloy, J., et al., "Thermodynamics of Movable Inductively Heated Seeds for the Treatment of Brain Tumors", *Medical Physics*, 18 (4), 794–803, (Jul./Aug. 1991).

Morrison, P.F., et al., "High–flow microinfusion: tissue penetration and pharmacodynamics", *American Journal of Physiology*, 266 (1) Part 2 of 2 Parts, R292–R305, (Jan. 1994).

Moseley, M.E., et al., "Anisotropy in diffusion–weighted MRL", *Magnetic Resonance in Medicine*, 19 (2), 321–326, (Jun. 1991).

Moseley, M.E., et al., "Magnetic resonance imaging of diffusion and perfusion", *Topics in Magnetic Resonance Imaging*, 3 (3), Magnetic Resonance Angiography, 50–67, (Jun. 1991).

Netti, P.A., et al., "Time–dependent behavior of interstitial fluid pressure in solid tumors: implications for drug delivery", *Cancer Research*, 55 (22), 5451–5458, (Nov. 15, 1995).

Nicholson, C., et al., "Diffusion from and iontophoretic point source in the brain: role of tortuosity and volume fraction", *Brain Research*, 169 (3), 580–584, (Jun. 29, 1979).

Nicholson, C., et al., "Hindered diffusion of high molecular weight compounds in brain extracellular microenvironment measured with integrative optical imaging", *Biophysical Journal*, 65 (6), 2277–2290, (Dec. 1993).

Nicholson, C., et al., "Ion diffusion modified by tortuosity and volume fraction in the extracellular microenvironment of the rat cerebellum", *The Journal of Physiology*, 321, 225–257, (1981).

Oldendorf, W.H., "Speculations on the Instrumentation of the Nervous System", *Proceedings of the San Diego Symposium for Biomedical Engineering*, 2, San Diego, CA, 274–280, (Jun. 19–21, 1962).

Penn, R.D., et al., "Intravascular intracranial EEG recording. Technical note", *Journal of Neurosurgery*, 38 (2), 239–243, (Feb. 1973).

Prabhu, S.S., et al., "Distribution of macromolecular dyes in brain using positive pressure infusion: a model for direct controlled delivery of therapeutic agents", *Surgical Neurology*, 50 (4), 367–375, (Oct. 1998).

Quate, E., et al., "Goniometric Motion Controller for the Superconducting Coil in a Magnetic Stereotaxis System", *IEEE Transactions on Biomedical Engineering* , 38 (9), 899–905, (Sep. 1991).

Ram, W., et al., "Heart catheterization in a neonate by interacting magnetic fields: a new simple method of catheter guidance", *Catherization and Cardiovascular Diagnosis*, 22 (4), 317–319, (Apr. 1991).

Ramos, P., et al., "Electro–Optic Imaging Chain for a Biplanar Fluoroscope for Neurosurgery: Magnetic Field Sensitivity and Contrast Measurements", *Optical Engineering* 32 (7), 1644–1656, (Jul. 1993).

Ramos, P., et al., "Microchannel Plate Image Intensifier Electron Dynamics in Magnetic Field", *Electronics Letters*, 27 (18), 1636–1638, (Aug. 29, 1991).

Ritter, R.C., et al., "Measurement of friction on straight catheters in in vitro brain and phantom material", *IEEE Transactions on Biomedical Engineering*, 45 (4), 476–485, (Apr. 1998).

Schmitt, F.O., "Molecular Regulators of Brain Function: A New View", *Neuroscience*, 13 (4), 991–1001, (1984).

Sendelbeck, S.L., et al., "Spatial Distribution of Dopamine, Methotrexate and Antipyrine During Continuous Intracerebral Microperfusion", *Brain Research*, 328 (2), 251–258, (Mar. 4, 1985).

Swanson, L.W., et al., "Autoradiographic Evidence for Pathways from the Medial Preoptic Area to the Midbrain Involved in the Drinking Response to Angiotensin II", *Journal of Comparative Neurology*, 178 (4), 645–659, (Apr. 15, 1978).

Wimberger, D.M., et al., "Identification of "Premyelination" by Diffusion–Weighted MRI", *Journal of Computer Assisted Tomography*, 19 (1), 28–33, (1995).

\* cited by examiner

Fig. 1
Fig. 2
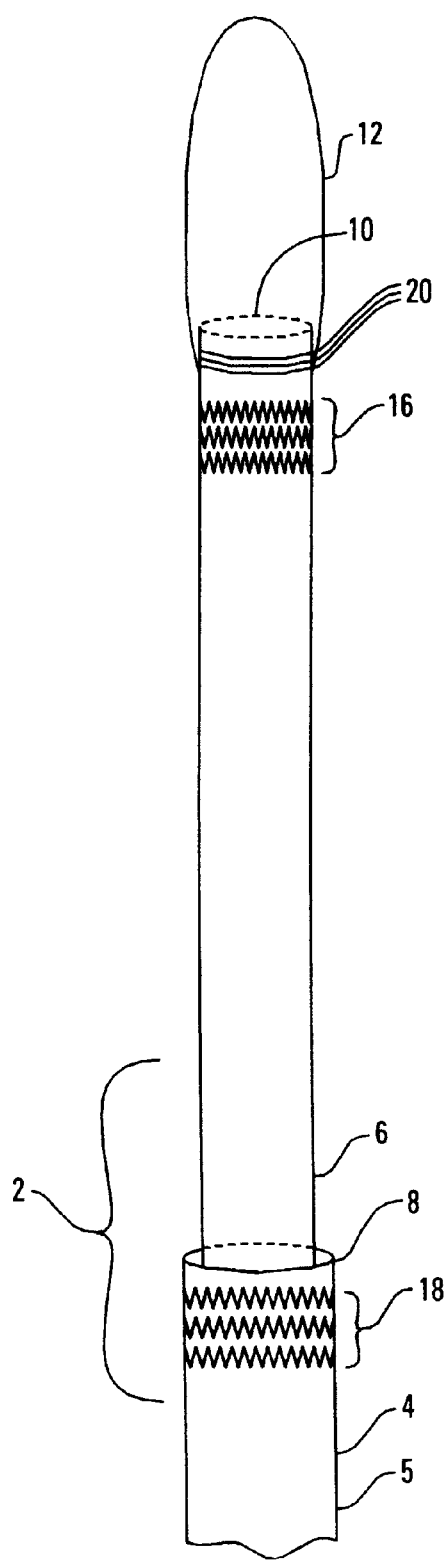
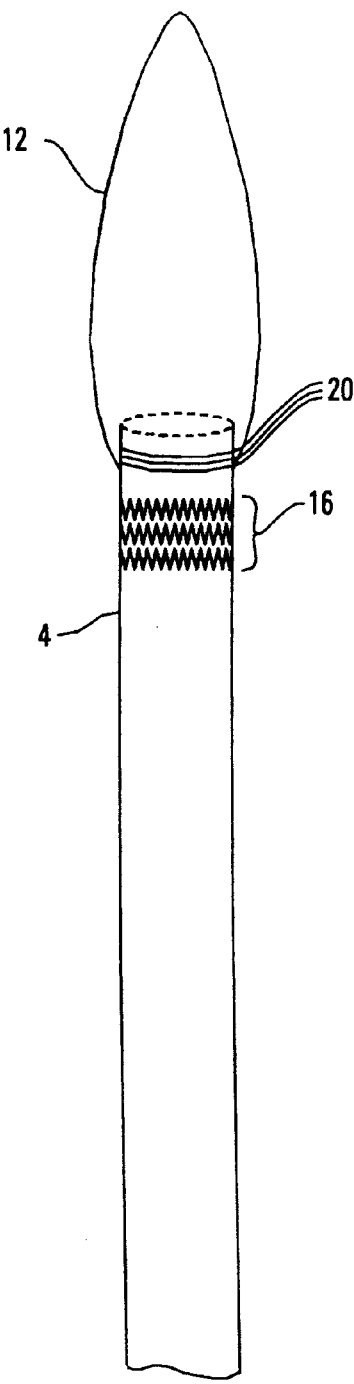

DEVICE AND METHOD FOR THE ENDOVASCULAR TREATMENT OF ANEURYSMS

BACKGROUND OF THE INVENTION

1. Field of the Invention

This invention relates to a device and method for endovascular treatment of aneurysms, particularly cerebral aneurysms. The method and device fills the volume of the aneurysm, provides material to the locality of the treatment which contains pharmacologically active agents, and may use intrumentalities and materials which are visible with magnetic resonance so that the procedure may be viewed in real time with magnetic resonance imaging systems.

2. Background of the Art

Autopsy studies have estimated that between 1.5% and 8% of the population have intracranial aneurysms. Between 60,000 and 80,000 cerebral aneurysms are diagnosed annually in the U.S., 20,000 to 30,000 following subarachnoid hemorrhage. The annual risk of an aneurysmal rupture is about 2%, producing a mortality rate of 50–60%. If untreated, 25–35% die of recurrent hemorrhage and, if there is patient survival, there is a significant deficit in neurological functions in 20–40% of the patients.

The traditional method for detecting an aneurysm and evaluating its vascular relationships is cerebral angiography, which has a morbidity rate of 1–2%. Non-invasive angiographic techniques with minimal morbidity have been developed recently. Magnetic resonance (MR) angiography (MRA), a form of magnetic resonance imaging (MRI), and computed tomography (CT) angiography (CTA), have demonstrated very high levels of detection (60–100%, depending upon the size of the aneurysm and the technique used). In particular, MRI/MRA have been very effective in detecting the asymptomatic, unruptured aneurysms. Both MRA and CTA also might be excellent techniques for following patients after surgical treatment. Unfortunately, the materials used for treatment frequently degrade the image, making evaluation of residual or recurrent aneurysm difficult or impossible.

The traditional method of treating patients with ruptured and unruptured cerebral aneurysms is surgical clipping, and approximately 15,000 of these surgical procedures are performed in the U.S. each year. Surgical mortality from clipping a previously ruptured cerebral aneurysm varies from 5% to 20% to, depending upon the site of the aneurysm and the neurological condition of the patient at the time of surgery. Surgical mortality for an unruptured aneurysm is from 2% to 10%.

Because of this high surgical mortality rate, a number of endovascular techniques have been developed to treat cerebral aneurysms. In 1974, Serbinenko first reported the successful treatment of intracranial aneurysms with detachable balloons. Using an endovascular approach similar to an angiogram, the balloon would be directed under fluoroscopic guidance to the aneurysm. If possible, the balloon would be placed inside of the aneurysm, leaving the parent artery intact. If the neck of the aneurysm were too large to entrap the balloon completely inside of the aneurysm, occlusion of the parent vein or artery would have to be performed. Large aneurysms typically required multiple balloons. Since 1974, a variety of detachable and nondetachable balloons made of a variety of materials, especially silicone and biocompatible polymeric latices, have been introduced. However, most aneurysms do not have the round or elliptical configuration of a balloon. Consequently, large aneurysms had to be filled with multiple balloons, leaving dead space for continued aneurysmal filling and subsequent rupture. The unfilled volumes could also allow for the development of clot in the aneurysmal remnant, enabling embolization to produce a stroke. Migration of a balloon from the aneurysm into the parent artery, or to a more distal branch of the parent system to produce a stroke, has also been reported in the literature. The use of balloons for direct aneurysm occlusion is therefor no longer performed. Parent artery occlusion using a detachable balloon is still a viable procedure, although the blood flow to the hemisphere may be compromised with such a procedure, producing a stroke.

Aneurysmal occlusion with microcoils is another endovascular technique. Very soft platinum microcoils have been developed recently, with and without fibers that induce thrombus formation. These soft microcoils are placed directly into an aneurysm, and the degree of occlusion is related to the ability to pack the coil mass tightly. A new variety of microcoil is the Guglielmi Detachable Coil (GDC) (U.S. Pat. No. 5,122,136). This utilizes an electrical current to induce thrombosis within the aneurysm. The current also breaks the solder-point connection between the guiding wire and the coil for a non-forceful detachment of the coil. While the morbidity (8%) and mortality (0.3 to 1.1%) are very low with this procedure, especially compared to conventional surgery, the electrically induced intra-aneurysmal thrombus is lysed and the coils compact over time, so that the permanence and therapeutic efficacy of the aneurysm occlusion is still unknown. More importantly, complete occlusion of an aneurysm at the time of initial placement of the coils ranges from 69% for small aneurysms with narrow necks, to 35% or less for larger aneurysms with wide necks. Aneurysms having wide necks relative to their diameters may not be even treatable with this technique. A wide neck allows the coils to herniate into the parent artery, which may produce unwanted parent artery occlusion and stroke. Therefore, aneurysms with wide necks usually must be treated surgically, with a higher morbidity/mortality rate than if an endovascular method had been available. The GDC also produces undesirable artifacts on MR scans, making it impossible to define an aneurysmal remnant or tissue injury in the region of the aneurysm. Lastly, electrolytic detachment of the GDC can result in migration of the solder remnants into the intracranial circulation.

In order to completely fill the lumen of an aneurysm, a device with the properties of a liquid would be preferable to more rigid devices such as the GDC coil. Liquid agents have been used for aneurysm ablation by directly injecting the agent into the aneurysm to produce a cast and subsequent thrombosis. An example of a liquid thrombotic material is cellulose acetate and bismuth trioxide dissolved in dimethylsulfoxide. On contact with blood in the aneurysm, the dimethylsulfoxide diffuses and the concentrating cellulose acetate polymer solidifies in the shape of the aneurysm within minutes. The liquid thrombotic material has a low viscosity and is easily injected through a small gauge catheter placed into the aneurysm via an endovascular approach. However, there are significant problems with this method of aneurysm ablation, including the distal migration of the polymer into normal vessels, producing stroke, and the slow leaking of the chemicals into the blood with dispersion to normal brain tissue, producing neurological dysfunction.

Other liquids, especially the cyanoacrylates (e.g., the iso-butyl and n-butyl forms), have been used for aneurysm occlusion. The cyanoacrylates polymerize in seconds after making contact with an ionic fluid like blood. The polymerization rate is difficult to control, however, and its rapidity makes precise and safe placement difficult. Like any liquid, the cyanoacrylate can flow out of the aneurysm into unwanted locations unless it can be contained.

The guidance of an endovascular catheter system, and the placement of an embolic agent or device into an aneurysm, currently is performed using x-ray fluoroscopy. Catheters and embolic agents are made from radio-opaque materials to allow visualization, and fluoroscopy allows the real-time visualization of the movement of the catheter system and the placement of the intra-aneurysmal occluding agents. However, there would be certain advantages to performing such a procedure under MR guidance. First, x-ray systems give significant levels of radiation to the lens of the eye during aneurysm ablation procedures. Radiobiological effects such as cataract formation may prove to be significant once enough time has elapsed for the effect of these relatively new procedures to become known. MR does not utilize ionizing radiation, and there are no known long-term adverse effects on biological tissues from MR, as used in a clinical MR imaging environment.

Second, x-ray fluoroscopy is a two-dimensional imaging technique. Multiple projections must be used to totally understand the anatomy of an aneurysm and its neck. Three-dimensional reconstruction of two-dimensional angiographic data has been performed, but the computer processing times are long. MR angiographic data, however, can be processed quickly into a 3-D image, allowing the accurate analysis of the aneurysm, the luminal volume that must be filled, and the size of the neck that must contain the filling (embolic) agent.

Third, x-ray fluoroscopy and angiography permit visualization of only the blood vessels, not the brain substance itself. X-ray fluoroscopy does not allow the visualization of complications such as hemorrhage or stroke during aneurysm therapy, nor can physiological processes, such as cerebral perfusion, be studied during this procedure which may effect cerebral blood flow and perfusion. MR, however, is a powerful technique that permits visualization of blood vessels (with MRA), acute hemorrhage and stroke (with various pulsing sequences of MRI), and cerebral perfusion (perfusion MR). Newly developed fast MR sequences even permit MR fluoroscopy.

Therefore, it would be advantageous if the guidance of the catheter system and the intra-aneurysmal embolic agents could be performed by both x-ray and MR systems. This would require that the catheters, guidewires, and embolic agents be visible by both x-ray and MR or that different parts of a single system be visible by x-ray or MR. If the guidance system of catheters and guidewires and the aneurysmal occluding agent contained different elements that were visible with MR or with x-ray, the procedure could be performed on a hybrid MR/x-ray fluoroscopy system in order to take advantage of the features of both imaging systems. New technologies such as intra-operative magnetic resonance imaging and nonlinear magnetic stereotaxis (Gillies et al. 1994), as two examples, will likely play increasingly important roles in optimizing endovascular treatment of neurological disorders. One type of high-speed MR imaging system combines high-resolution MR imaging with conventional X-ray fluoroscopy and digital subtraction angiography (DSA) capability in a single hybrid unit. The real-time imaging capability of this combination of techniques makes it possible to use high-speed MR imaging to observe the effects of specific interventional procedures, such as thrombotic occlusion of aneurysms.

Visualization of an endovascular device could depend upon its being coated with an MR contrast agent, or upon its effect on the MR image by nature of its chemical makeup. However, compounds and materials considered MR compatible, and even MR contrast agents, can produce significant distortion artifacts that obscure the brain and blood vessel anatomy and physiology. Initial attempts to visualize endovascular devices in MR imaging were based on passive susceptibility artifacts produced by the device when exposed to the MR field. U.S. Pat. Nos. 5,154,179 and 4,989,608 to Ratner disclose the incorporation of paramagnetic material into endovascular devices to make the devices visible under MR imaging. However, these patents do not provide for artifact-free MR visibility in the presence of rapidly alternating magnetic fields, such as would be produced during echo-planar MR imaging pulse sequences used in real-time MR guidance of intracranial drug delivery procedures. Nor do these patents teach a method for monitoring with MR visible catheters the outcomes of therapeutic interventions. Ultrafast imaging sequences generally have significantly lower spatial resolution than conventional spin-echo sequences. Image distortion may include general signal loss, regional signal loss, general signal enhancement, regional signal enhancement, and increased background noise. The magnetic susceptibility artifact produced by the device must be small enough not to obscure surrounding anatomy, or mask low-threshold physiological events that have an MR signature, and thereby compromise the physician's ability to perform the intervention.

An improved method for passive MR visualization of implantable medical devices has recently been disclosed by Werne (Pending U.S. patent application Ser. No. 08/554446, ITI Medical Technologies). That invention minimizes MR susceptibility artifacts, and controls eddy currents in the electromagnetic scattering environment, so that a bright "halo" artifact is created to outline the device in its approximately true size, shape, and position. In the method of the invention disclosed by ITI, an ultra thin coating of conductive material comprising 1–10% of the thickness of the material being imaged—typically about 250,000 angstroms—is applied. By using a coating of 2,000–25,000 angstroms thickness, ITI has found that the susceptibility artifact due to the metal is negligible due to the low material mass. At the same time, the eddy currents are limited due to the ultra-thin conductor coating on the device.

Exemplary of methods for active MR visualization of implanted medical devices is U.S. Pat. No. 5,211,165 to Dumoulin et al., which discloses an MR tracking system for a catheter based on transmit/receive microcoils positioned near the end of the catheter by which the position of the device can be tracked and localized. U.S. Pat. No. 5375,596 to Twiss et al., discloses a method for locating catheters and other tubular medical devices implanted in the human body using an integrated system of wire transmitters and receivers. U.S. Pat. No. 4,572,198 to Codrington also provides for conductive elements, such as electrode wires, for systematically disturbing the magnetic field in a defined portion of a catheter to yield increased MR visibility of that region of the catheter. However, the presence of conductive elements in the catheter also introduces increased electronic noise and the possibility of Ohmic heating, and these factors have the overall effect of degrading the quality of the MR image and raising concerns about patient safety. Thus, in all of these examples of implantable medical probes, the presence of MR-incompatible wire materials allows the possibility of causing large imaging artifacts. The lack of clinically adequate MR visibility and/or imaging artifact contamination caused by the device is also a significant potential problem for most commercially available catheters, microcatheters and shunts.

It is also important that endovascular devices used under MR guidance are MR-compatible in both static and time-varying magnetic fields. Although the mechanical effects of the magnetic field on ferromagnetic devices present the greatest danger to patients through possible unintended movement of the devices, tissue and device heating may also result from radio-frequency power deposition in electrically conductive material located within the imaging volume. Consequently, all exposed areas of the device, such as the cables, wires, surfaces and other devices positioned within the MR imaging system must be made of materials that have properties that make them compatible with their use in human tissues during MR imaging procedures.

A variety of implantable endovascular devices have been described, as follows:

U.S. Pat. No. 3,868,956 to Alfidi discloses a stent-like vessel expander or expandable filter made of a shape memory metal, such as an alloy containing nickel and titanium (Nitinol). An external woven (e.g., Dacron) sleeve is expanded by an internal Nitinol structure. The expansile appliance is initially formed in an expanded configuration and is then deformed to a straight-line configuration for implantation. Once placed in a desired position, the device is heated, causing it to resume its expanded configuration. In one embodiment, the appliance in its expanded configuration comprises a coil of wire used to expand or enlarge a vessel. However, the device is not specifically designed to be MR-visible and there is no mention of using the device as an endovascular therapy for aneurysms.

U.S. Pat. No. 4,503,569 to Dotter discloses the use of a coil of shape memory metal (Nitinol) as an endovascular stent. The endovascular prosthesis includes a helically wound coil having a generally tubular shape. After placement of the stent within a body blood vessel and upon heating of the prosthesis beyond 115 degrees C., it expands so as to become firmly anchored to the inside wall of the blood vessel. After expansion, the diameter of the lumen of the prosthesis is approximately equal to the diameter of the blood vessel. There is no reference to the application of this device for the treatment of cerebral aneurysms, nor is it MR visible.

U.S. Pat. No. 4,727,873 to Mobin-Uddin discloses an endovascular embolus trap, which is comprised of multiple filamentary loops extending outwardly from a central column. The device is inserted into blood vessels to engage and hold blood clots. Although obstructed vascular conditions are mentioned, there is no reference to applications for aneurysm therapy.

U.S. Pat. No. 4,994,071 to MacGregor discloses a bifurcating or branching stent in which a balloon expanding technique is used to expand the stent from insertion size to implant size. The balloon is then deflated and withdrawn from the vessel. Although obstructed vascular conditions are mentioned, there is no reference to applications for aneurysm therapy.

U.S. Pat. No. 4,998,539 to Delsanti discloses a method of using a removable device for promoting healing of detached flaps from the arterial wall. The expansile/contractile device is formed of interwoven wires. Remote actuation is used to cause expansion, and after healing, to cause contraction. It is thus distinguishable from the method and device of the present invention.

U.S. Pat. No. 5,035,706 to Gianturco discloses a specialized spring-expansible stent construction employing eyes formed at the bends of a zig-zag spring stent construction, as a variant of the Gianturco Z-form spring stent. However, the device is not specifically designed to be MR-visible and there is no mention of using the device as an endovascular therapy for aneurysms.

U.S. Ser. No. 07/788,799 to Clouse discloses a "Method and Device for Performing Endovascular Repair of Aneurysms". However, the device is not specifically designed to be MR-visible.

U.S. Pat. No. 5,102,401 to Lambert et al. discloses an expandable catheter consisting of hydrophilic thermoplastic elastomeric polyurethane with a hydrophobic polymer coating. However, the device is not specifically designed to be MR-visible and there is no mention of using the device as an endovascular therapy for aneurysms.

U.S. Pat. No. 5,102,402 to Dror et al. discloses a balloon angioplasty catheter with a releasable drug-containing microcapsule coating on the balloon surface. However, device is not specifically designed to be MR-visible and there is no mention of using the device as an endovascular therapy for aneurysms.

U.S. Pat. No. 5,304,194 to Chee et al. discloses a vascular occlusion coil with multiple attached fibrous elements. However, the device is not specifically designed to be MR-visible.

U.S. Pat. No. 5,304,197 to Pinchuk et al. discloses a fabrication method for balloons as medical devices. However, the device is not specifically designed to be MR-visible and there is no mention of using the device as an endovascular therapy for aneurysms.

U.S. Pat. No. 5,304,199 to Myers discloses an elastomeric balloon for creating a cleft through a total blockage in a vascular structure. However, the device is not specifically designed to be MR-visible and there is no mention of using the device as an endovascular therapy for aneurysms.

U.S. Pat. No. 5,108,407 to Geramia et al. discloses a method and apparatus for placement of an embolic coil at an intravascular lesion site. The invention includes a heat sensitive adhesive to reversibly bond the coil to a connector. However, the device is not specifically designed to be MR-visible and there is no mention of using the device as an endovascular therapy for aneurysms.

U.S. Pat. No. 5,217,483 to Tower discloses an intravascular radially expandable stent. However, the device is not specifically designed to be MR-visible and there is no mention of using the device as an endovascular therapy for aneurysms.

U.S. Pat. No. 5,108,420 to Marks discloses an aperture occlusion device using a catheter-based wire occluder. However, the device is not MR-visible and there is no mention of using the device as an endovascular therapy for aneurysms.

U.S. Pat. No. 5,258,020 to Froix discloses a method of using an expandable polymeric stent with memory. However, the device is not MR-visible and there is no mention of using the device as an endovascular therapy for aneurysms.

U.S. Pat. No. 5,104,403 to Brotzu discloses a low porosity vascular prosthesis with hormone-producing cells contained within microcapsules placed in the walls of the prosthesis. However, the device is not MR-visible and there is no mention of using the device as an endovascular therapy for aneurysms.

U.S. Pat. No. 5,221,261 to Termin discloses a radially expandable intravascular fixation device and a method for securing the surface of the device to a tissue wall. However, the device is not MR-visible and there is no mention of using the device as an endovascular therapy for aneurysms.

U.S. Pat. No. 5,158,548 to Lau discloses a method and system for delivery of an expandable intravascular stent. However, the device is not MR-visible and there is no mention of using the device as an endovascular therapy for aneurysms.

U.S. Pat. No. 5,234,456 to Silvestrini discloses an intravascular stent with a semi-permeable membrane wall into which is placed a hydrophilic material capable of absorbing a liquid to increase the volume of the stent. However, the device is not specifically designed to be MR-visible and there is no mention of using the device as an endovascular therapy for aneurysms.

U.S. Pat. No. 5,234,457 to Anderson discloses an intravascular stent impregnated with a material that can initiate expansion of the stent into the vessel wall. However, the device is not specifically designed to be MR-visible and there is no mention of using the device as an endovascular therapy for aneurysms.

U.S. Pat. No. 5,342,303 to Ghaerzadeh discloses balloon catheters and related medical devices having non-occluding balloon inflation-deflation apertures. However, the device is not specifically designed to be MR-visible and there is no mention of using the device as an endovascular therapy for aneurysms.

U.S. Pat. No. 5,263,963 to Garrison discloses an expandable cage catheter for repairing a damaged blood vessel. However, the device is not specifically designed to be MR-visible and there is no mention of using the device as an endovascular therapy for aneurysms.

U.S. Pat. No. 5,330,500 to Song discloses a self-expanding endovascular stent with silicone coating. However, the device is not specifically designed to be MR-visible and there is no mention of using the device as an endovascular therapy for aneurysms.

U.S. Pat. No. 5,133,733 to Rasmussen discloses a collapsible filter for introduction into a blood vessel of a patient. However, the device is not specifically designed to be MR-visible and there is no mention of using the device as an endovascular therapy for aneurysms.

U.S. Pat. No. 5,037,427 to Harada discloses a method of implanting and removing an endovascular stent having a two-shape memory that is activated using a cooling liquid. However, the device is not specifically designed to be MR-visible and there is no mention of using the device as an endovascular therapy for aneurysms.

U.S. Pat. No. 4,994,069 to Ritchard discloses a vascular occlusion coil that uses a memory metal. However, the device is not specifically designed to be MR-visible and there is no mention of using the device as an endovascular therapy for aneurysms.

U.S. Pat. No. 5,370,691 to Samson discloses an intravascular polymeric inflatable stent. However, the device is not specifically designed to be MR-visible and there is no mention of using the device as an endovascular therapy for aneurysms.

U.S. Pat. No. 5,368,566 to Crocker discloses a temporary stent for maintaining blood vessel patency. However, the device is not specifically designed to be MR-visible and there is no mention of using the device as an endovascular therapy for aneurysms.

U.S. Pat. No. 5,378,239 to Termin discloses a radially expandable fixation device constructed of recovery metal. However, the device is not specifically designed to be MR-visible and there is no mention of using the device as an endovascular therapy for aneurysms.

U.S. Pat. No. 5,383,928 to Scott discloses a polymer stent sheath for local intravascular drug delivery. However, the device is not specifically designed to be MR-visible and there is no mention of using the device as an endovascular therapy for aneurysms.

U.S. Pat. No. 5,250,071 to Palermo discloses a detachable intravascular embolic coil assembly that uses interlocking clasps. However, the device is not specifically designed to be MR-visible and there is no mention of using the device as an endovascular therapy for aneurysms.

U.S. Pat. No. 5,334,210 to Gianturco discloses a vascular occlusion assembly comprised of a bag of foldable material, and an internal catheter activator. However, the device is not specifically designed to be MR-visible.

U.S. Pat. No. 5,382,260 to Dormandy discloses an embolization device and apparatus including an introducer cartridge. However, the device is not specifically designed to be MR-visible.

U.S. Pat. No. 5,382,261 to Palmaz discloses a method and a tubular apparatus for occluding blood vessels. However, the device is not specifically designed to be MR-visible and there is no mention of using the device as an endovascular therapy for aneurysms.

A problem with the use of platinum microcoils, such as the GDC, is the lack of stimulation of scar formation within the aneurysm and an endothelial lining over the mouth of the aneurysm, insuring complete and permanent occlusion. U.S. Pat. No. 5,171,217 to March describes the delivery of several specific compounds by direct injection of microcapsules or microparticles using multiple-lumen catheters, such as disclosed by Wolinsky in U.S. Pat. No. 4,824,436. Incorporation of pharmaceutical agents into thin surface coatings during manufacture of a device will allow the agent to diffuse out of the coating at a controlled rate. The coating can incorporate natural or synthetic materials, such as antibiotics, thrombus-inducing or anti-thrombus chemicals, and agents such as fibroblastic and endothelial growth factors. U.S. Pat. No. 5,120,322 to Davis et al., describes the process of coating the surface layer of a stent or shunt with lathyrogenic agent to inhibit scar formation during reparative tissue formation, thereby extending exposure to the drug agent. U.S. Pat. Nos. 3,705,938 and 3,857,934 to the Herculite Protective Fabrics Corporation describe the incorporation of a chemical agent into a thin surface coating to allow diffusion of the chemical at a controlled rate.

However, exposed coatings on catheters which contain drug agents usually require some type of protective sheath that must be removed from the catheter before the drug can be released from the coating. The sheath and any catheter components required to manipulate the sheath greatly increase the profile of the catheter, make it less flexible, and thereby limit the variety of applications for which the drug delivery system can be employed, particularly for cerebral aneurysm treatment. In addition, binders or adhesives used in catheter coatings may significantly dilute the concentration of the therapeutic agent. The therapeutic agent could be bonded loosely to the catheter with a material such as macroaggregated albumin that is sensitive to thermal energy for release of the agent. U.S. Pat. No. 5,087,256 to Taylor describes an example of a catheter-based device that converts radiofrequency energy to thermal energy. However, the thermal energy required for release could cause damage to the blood vessel.

U.S. Pat. No. 5,470,307 to Lindall discloses a low-profile catheter system with an exposed coating containing a therapeutic drug agent, which can be selectively released at remote tissue sites by activation of a photosensitive chemical linker. In the invention disclosed by Lindall, the linker is attached to the substrate via a complementary chemical group, which accepts a complementary bond to the therapeutic drug agent. The drug agent is, in turn, bonded to a molecular lattice to accommodate a high molecular concentration per unit area. Ancillary compounds such as markers or emitters may also be attached to the drug agent so its location and movement can be monitored.

Another problem with current interventional therapies for treatment of cerebral aneurysms is the release of an embolic agent or device from the catheter transporting it to the aneurysm. The GDC platinum microcoil is attached to a transporting steel microguidewire by a small solder joint, and is detached when an electric current is passed through the steel microguidewire to lyse the solder joint. The time for this electrolytic release mechanism becomes progressively prolonged as more platinum coils are placed into the aneurysm. Detachable balloons, filled with either a fluid or a solid polymer, are detached when the transporting catheter is pulled back. The distended balloon exerts radial forces on the luminal walls of the aneurysm or blood vessel, and a special valve in the neck of the balloon closes as the catheter is withdrawn in order to keep the balloon distended. However, this technique exerts undo forces on the aneurysm, which may cause it to rupture. The direct placement of balloons into aneurysms, requiring such a release mechanism, is no longer performed. There is no other container to hold a polymerized fluid that could be placed inside an aneurysm, nor a mechanism to release such a container, in the current practice of endovascular therapy.

SUMMARY OF THE INVENTION

The present invention comprises a method and a device for treating hemodynamically significant aneurysms, particularly those of the intracranial circulation, while the procedure is being performed under image guidance mechanisms, especially either X-ray fluoroscopy and/or real-time magnetic resonance (MR) imaging guidance. A device for the practice of the present invention may comprise, for example, an association of a catheter and guidewire, a microcatheter, and a parachute element. A preferred construction comprises an association of a catheter and guidewire, a microcatheter, a parachute element, and a balloon. A preferred method of associating the respective elements would comprise having the balloon (if used) securely (less preferably detachably) attached to the catheter and the parachute element detachable from the microcatheter. The microcatheter may be carried through an opening in the balloon catheter, or may be separate, along the side of the balloon catheter, for appropriate placement during the procedure. Preferably the parachute element comprises an MR-visible, parachute-shaped device, containing a plurality of elongated filamentary loops made of flexible and expandable materials, such as an elastomeric hydrogel, polymeric materials such as polyamide mesh, Nitinol mesh (or a mesh of other biocompatible materials), or other expansile material. The parachute element, during the procedure, is radially expanded from a closed position while the device is within the lumen of the aneurysm. The device may be subsequently fixed, preferably permanently fixed, into surface contact with the aneurysm wall when the device is filled or partially filled with materials, such as a polymer material. MR visibility of the occlusive device is achieved using an MR-visible coating, filler, embedded elements or attachments within or on the composition of the device, permitting MR imaging of the device during and after the occlusion procedure. Detachment of the aneurysm occlusion device from the transport catheter, hollow wire, or hollow tube can be achieved by one or more of the following methods. The methods include, but are not limited to mechanical decoupling, hydration of the device/catheter or device/wire interface, by thermal exchange coupling or transduction, irradiation initiated change in adherent compositions, predetermined memory pH or osmolality changes, or by any other mechanical, chemical, electrical, and/or radiation techniques which can release the aneurysm occlusion device. The parachute device induces permanent occlusion of the aneurysm by timed delivery of biologic modifying drugs that promote fibroblast ingrowth and collagen formation within the aneurysm, and endothelial proliferation over the mouth of the aneurysm. The transporting microcatheter, the hollow tube or wire to which the parachute is attached, and the forming balloon catheter may have their surfaces impregnated with an MR-visible contrast material, or some other MR visible device may be attached to them. This will enable continuous MR visualization of their position during the filling of the parachute. The subject invention provides a method for the use of embolic materials under one or both of X-ray or MR-imaging guidance in ways different from those taught in the prior art.

BRIEF DESCRIPTION OF THE DRAWINGS

FIG. 1 shows a microcatheter-parachute assembly according to the present invention with a non-expanded parachute attached to a hollow guidewire or hollow tube that has been passed through a microcatheter.

FIG. 2 shows a microcatheter-parachute assembly according to the present invention with a non-expanded parachute directly attached to the catheter.

DETAILED DESCRIPTION OF THE INVENTION

Figure 3:
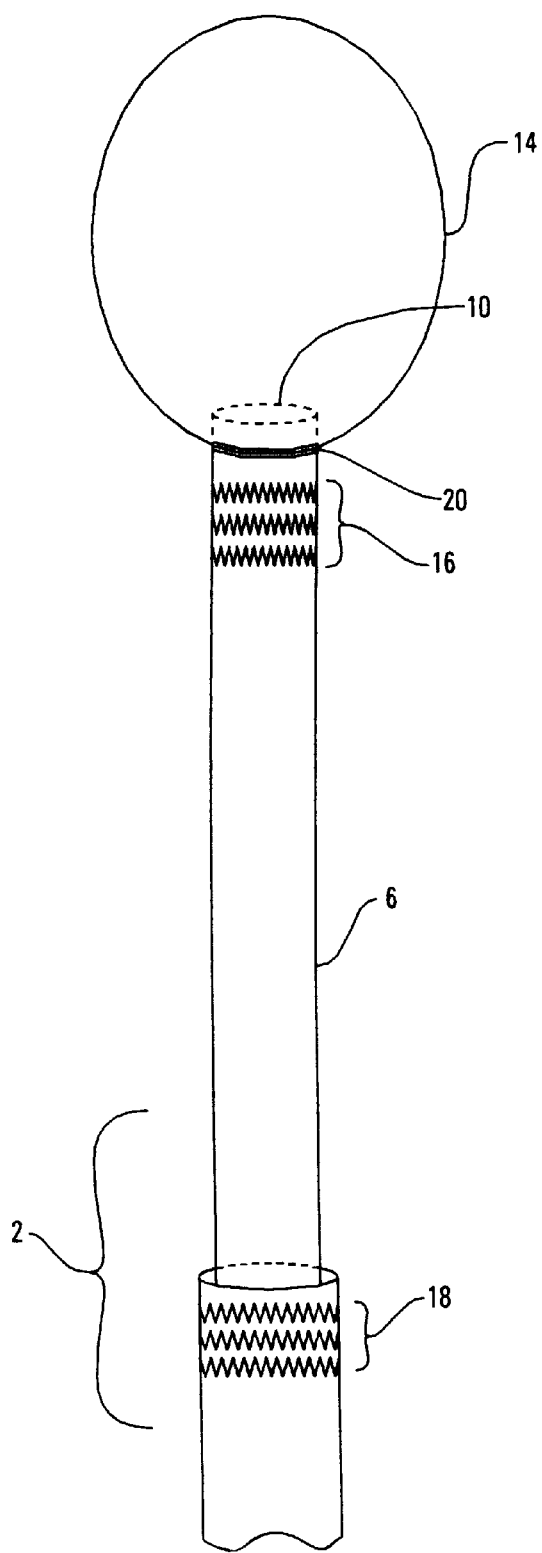
FIG. 3 shows a microcatheter-parachute assembly according to the present invention with an expanded parachute attached to a hollow guidewire or hollow tube.

The are a number of distinct differences between the practice of the present invention in comparison to prior art medical techniques for the repair or treatment of aneurysms. The occlusion device of the present invention, referred to herein as a parachute, is clearly different from the microcoils, coils, and balloons that have been previously described. The term "expansile" is used to denote one aspect of the difference in the following manner. Balloons are elastically expandable, the composition of the balloon itself undergoing elastic stretching when internal fluid pressure exceeds the external surface pressure. An expansile material, on the other hand, when subjected to internal fluid pressure which exceeds the external surface pressure by at least 0.1, 0.2 or 0.5 pounds per square inch (for example), will expand to approximately the structural limits of the shape of the parachute, with less than 10% or less than 5% of the enlargement from the retracted to the expanded state occurring from any elastic extension or stretching of the composition of the parachute. This expansion may be in the manner of an expanding accordion effect. The parachute may be folded upon itself, twisted upon itself, or arranged in any other manner that will allow it to reconfigure into its full size and shape upon the application of reasonable fluid pressure within it cavity. It is preferred that less than 2%, and more preferably that less than 1% of the expansion from the fully retracted state to the fully expanded state derive from elastic elongation of the parachute composition, as opposed to unfolding of a compacted or folded structure. The parachutes, for example, may be partially constructed from coils and microcoils which are spring-like, open devices, made of MR-compatible materials, which have their own intrinsic shape and are packed into the lumen of the aneurysm. The spring-like coils of the parachute may extend, but without elastic deformation of the coil material. The balloons, on the other hand, are elastomeric materials that distend (elastically deform) essentially equally (with uniform thickness of the balloon material) when internal pressure (within the balloon cavity) is provided. The pressure is equally applied against all interior surfaces of the balloon, and thereby uniformly expanding the balloon by stretching the material. This assumes a uniform thickness in the balloon and an equal distribution of surface pressure (e.g., there is no restrictive contact between the surface of the balloon and another surface).

The parachute of the present invention is intended to have little if any elasticity in the components of the device which are essential to distribution of the parachute within the aneurysm. The parachute may have some significant apparent gross elasticity because of the structure of the material (e.g., knitted, woven, braided, folded, telescoping, accordion components, etc.). The parachute should have little or no structural elasticity because of the composition of the materials, even though most materials, including polymers and metals, have some native elasticity. Thus, materials with less than 10% elasticity (e.g., the percent of expansion of one dimension) when one kilogram force is applied along the length of a square centimeter segment is desired. Preferably less than 7.5% elasticity is present, and more preferably less than 5%, less than 3% and less than 1% elasticity is desired in a square centimeter segment. Examples of useful materials include Nitinol fabric (knitted and woven), polyamide fabric (knitted or woven), or fabrics and films of biocompatible materials (e.g., metals, metal oxides, ceramics, polymers, composites and the like). Films with significant texturing in them (e.g., such as done with crepe paper or other extensible texturing) are also useful. The materials should not decompose within the body (within the time frame when the device is intended to remain within a living patient) and should not contain toxic or highly allergenic materials that would leach out of the material (as would some plasticizers in polymeric materials) or form upon eventual decomposition or exposure to the expected fluids within the body of a patient.

This container should be made of a material that could be imaged (detectable) by both x-ray and MR. Visibility by MR without artifact production is extremely important so that the patient may be imaged to evaluate the possibility of future revasculation and recurrent patency of the aneurysm, without resorting to traditional angiography with its attendant complication rate. Complications following aneurysmal rupture or the treatment of the aneurysm, or for other current or future neurological problems, would be best evaluated with MR imaging, since it is the most sensitive and specific imaging technique for evaluating the brain and its many disorders. The use of an aneurysm clip usually prohibits a patient from being imaged with MRI because of the possibility that the magnetic field could dislodge the clip, in addition to the degradation of the image by the clip. The quality of an MRI is frequently degraded by the Guglielmi Detachable Coils (GDC) in an aneurysm, requiring the use of CT or other less specific imaging technique. Thus, the aneurysmal occluding agent should be MR-visible and MR-compatible yielding minimal, if any, image distortion. MR visibility could be provided for example by the use of MR responsive microcoils or impregnating or coating portions of the device with MR visible materials.

There should be some extensibility and flexibility in the parachute material as it must be able to conform to the various shapes and dimensions of the interior lumen of the aneurysm. This is in contrast to balloons, which essentially uniformly expand in a spherical or ellipsoid manner, and fill the shape with only minor variations for those shapes. As pressure is increased to attempt to force a balloon into conformance with spaces left between the moderately inflated balloon and the walls of the aneurysm where contact has not been made, excess force inadvertently may be applied to weak areas of the aneurysm walls where initial contact had been made. This may result in rupture of the aneurysm. The lower elasticity, but greater ability of the parachute materials of the present invention to conform to a non-uniform shape allows for a more even distribution of pressure and greater volume occupation filling of an aneurysm. With materials of high conformability, as opposed to materials of high elasticity, the materials with high conformability can conform to a shape with more equal distribution of forces against the surface to which conformation is being effected.

Because there is limited elasticity in the parachute, a variety of parachute volumes are manufactured in order to adapt to the various volumes of aneurysms, ranging from a few cubic millimeters to a few cubic centimeters.

The parachute should be able to completely volume occupy the space within an aneurysm, and be easily expanded so as not to rupture the aneurysm. The parachute functions best by being filled with a liquid such as a hardenable polymer. A container for a liquid would keep that liquid within the aneurysm, but such a container would have to be extremely flexible. The container would have to expand from a contracted state, as it is delivered through blood vessels of a few millimeters in size into an aneurysm with a neck as small as 1–2 millimeters. In its expanded state, it would fill an aneurysm ranging from 3 to 25 or more millimeters in diameter. This container, therefore, would have to be flexible, expansile, and of minimal porosity in order to contain the liquid. Some porosity is tolerable or even desirable to allow for any entrapped gases within the parachute to be expelled through the pores, but without allowing hardenable liquid to flow through the pores before it is hardened. Control of pore size and hydrophilicity of the parachute around the pores are techniques to be used in controlling the effectiveness of any porosity.

Where a fabric or porous film is used as the parachute material, the material should have pore sizes small enough to restrain flow of any particulate material, colloidal solution, or polymer in the material injected or inserted into the parachute to fill and secure it. For example, if a colloidal dispersion of polymer having polymer particles with average dimensions of 1 micron are to be used (with a±25% particle size distribution), the pore size or mesh, opening size of the fabric, or film should be less than 0.75 microns to assure restraint of the particles. This addresses one of the problems encountered by direct injection of a polymer into the aneurysm and flow of this substance into the blood stream and occlusion of healthy vessels. It also avoids a problem encountered where an open stent is used in the arterial lumen across the mouth of the aneurysm to close that mouth or support injected hardenable liquid placed into the aneurysm.

The fabric, as noted above, should be highly conformable. This can be done by balancing the flexibility of the material used (both the fineness of fibers used in the fabric as well as the native flexibility of the material in the fiber) and the tightness of the fabric construction. Thus, fine fibers can be used in a tight knit or weave (or non-woven construction, with fusion or adhesion of the fibers at the crossover points), or thicker fibers with less tight weaves or knits (or fewer bonding sites in a non-woven construction) may be used. Films with large numbers of small pores (a foraminous film or gossamer-like fabric) could also be used. The composition of the film material and the number, size and distribution of the pores would assist in controlling the conformation of the parachute material to mold to the shape of the aneurysm.

One aspect of this invention is the provision of an endovascular procedure to treat aneurysms, especially narrow-neck aneurysms, comprising the following steps:

a) determine the volume of the aneurysm, as by using digital subtraction angiography (DSA), MRA, or CTA, and select the parachute system of a size and configuration appropriate to the volume of the aneurysm, b) catheterize the aneurysm, preferably using a microcatheter and microguidewire, c) remove the microguidewire and replace the microguidewire with a hollow guidewire or hollow tube with an attached parachute, d) inject liquid (e.g., saline solution) to partially enlarge or engage the parachute within the aneurysm, e) slowly inject polymer to completely fill the parachute within the confines of the aneurysmal lumen, f) verify isolation of the aneurysm from the parent blood vessel using radiologic imaging techniques; and g) detach the parachute/polymer from the hollow guidewire or hollow tube. The term "guidewire" usually implies its fabrication from some type of metal, which may be or may not visible with x-ray imaging devices. Because a metal may produce unwanted artifacts during MR imaging, if the procedure were to be performed with such guidance, the use of an MR-compatible hollow tube or artifact-free material (e.g., ceramic, polymer or composite which is not responsive to MR-imaging) may be preferable. It may be possible to catheterize the aneurysm by using the parachute/hollow guidewire/tube without resorting to the standard microguidewire by appropriate design of the hollow guidewire/tube with the parachute attached thereto. It may also be possible to catheterize the aneurysm with a catheter to which the parachute is directly attached. In this case, a microguidewire may be placed inside the catheter to assist in the catheterization. This microguidewire is removed before the injection of saline and/or polymer, A second aspect of this invention is the provision of an endovascular procedure which will effectively and safely treat wide-neck aneurysms. This may be accomplished by steps which:

a) determine the volume of the aneurysm, as by using DSA, MRA, or CTA, and select the parachute system of a size appropriate for the volume of the aneurysm.

b) catheterize the aneurysm, preferably using a microcatheter and microguidewire, c) remove the microguidewire and replace the microguidewire with a hollow guidewire or hollow tube with an attached parachute, d) inject liquid (e.g., saline solution) to partially enlarge or engage the parachute within the aneurysm, e) introduce a non-detachable balloon catheter having two lumens, and place it across the mouth of the aneurysm, within the lumen of the parent cerebral artery, f) infuse the patient's heparinized blood through the central lumen of the balloon catheter to maintain distal cerebral perfusion, g) inflate the balloon through the lumen of the catheter leading to the balloon, to cover a large majority (e.g., greater than 70%–90%) of the neck of the aneurysm, forming a firm structure against which the parachute may expand, yet leaving a space for the egress of blood within the aneurysm as the parachute expands, h) slowly inject the polymer into the parachute so that the parachute completely fills the aneurysm, i) verify isolation of the aneurysm from the parent blood vessel using radiologic imaging methods, j) detach the parachute/polymer from the hollow guidewire.

It may be possible to use the parachute/hollow guidewire/tube to catheterize the aneurysm without resorting to the standard microguidewire by appropriate design of the hollow guidewire/tube with the parachute attached thereto. It also may be possible to catheterize the aneurysm with a catheter to which the parachute is directly attached. In this case, a microguidewire may be placed into the catheter to aid the catheterization process, and removed before injection of saline and/or polymer.

A third aspect of this invention is the provision of an endovascular procedure to effectively and safely treat hemodynamically significant aneurysms involving the carotid and vertebral arterial distributions in human patients with asymptomatic and symptomatic cerebrovascular disease, in particular aneurysms inaccessible by direct surgery.

A fourth aspect of this invention is to provide an aneurysm occlusion device that totally fills the volume of an aneurysm, whether the aneurysm has a narrow or a wide neck, whatever the size, volume, and configuration of the aneurysm.

A fifth aspect of this invention is to provide an MR-visible occlusion device to treat aneurysms, said device allowing artifact-free MR imaging during and after use of the device.

A sixth aspect of this invention is to provide an MR-visible occlusion device to treat aneurysms under MR and/or x-ray imaging guidance.

A seventh aspect of this invention is to provide an aneurysm occlusion device that is detachable by mechanical, electrical, radiation-initiated, or thermal means.

A eighth aspect of this invention is to provide an aneurysm occlusion device that has the physicochemical characteristics to induce thrombus formation, collagen formation, fibroblast growth, and endothelial growth within the aneurysm.

A ninth aspect of this invention is to provide an aneurysm occlusion device to be used in conjunction with local pharmacologic therapies to reduce morbidity and mortality associated with stroke, intracranial vasospasm, and subarachnoid hemorrhage resulting from cerebral aneurysm rupture.

A tenth aspect of the present invention is to permit the maintenance of cerebral perfusion during the treatment of aneurysms that may require temporary parent artery occlusion. This can even be done with wide-neck aneurysms in the following manner. A microcatheter with the parachute attachment is inserted into the wide-neck aneurysm. A second catheter with a non-detachable balloon element is then inserted into the parent vessel. This catheter has two lumens, one in the center to allow passage of a fluid or a wire from one end of the catheter to the other, and a second lumen leading to the balloon, providing for its inflation or deflation. A variety of balloon lengths are available, and the length is selected so that it will cover the mouth of the aneurysm. The balloon is placed over the mouth of the aneurysm and inflated so that the majority (70%–90%) of the mouth of the aneurysm is covered. This provides a surface against which the parachute may expand. A small portion of the mouth is left uncovered so that blood within the aneurysm may escape as the parachute is expanded, preventing too much pressure within the aneurysm with parachute expansion. The catheter supporting the balloon allows blood flow to continue through the parent vessel for cerebral perfusion distal to the inflated balloon, thereby preventing flow-related ischemia. Once the polymer has been injected into the parachute and has hardened sufficiently, the balloon is deflated and the catheter with non-detachable balloon is removed. The parachute is then detached from the hollow microguidewire or hollow tube (or microcatheter if the parachute had been attached directly to it).

The physical profile and operating characteristics of the MR-visible aneurysm occlusion device may be summarized with reference to the figures as follows:

FIG. 1 shows an assembly of a microcatheter device 2 according to the present invention. The microcatheter device 2 comprises a microcatheter tube 4 (usually having dimensions in the range of from 0.15 to 2.50 mm diameter) containing a flexible hollow wire or tube 6 which can be telescoped out of the microcatheter 4 at microcatheter tip 8. The diameter of the hollow wire/tube 6 should be relatively close to that of the microcatheter, yet be sufficiently small enough to fit within and slide freely through the microcatheter 4. The outside diameter of the hollow wire/tube 6 may be from 10% to nearly 100% of the inside diameter of the microcatheter 4. A non-expanded parachute 12 is connected to the hollow wire/tube 6 so that the parachute extends over opening 10 of the hollow wire/tube 6. The parachute 12 is attached to the hollow wire/tube 6 by an adhesive or other attachment process that may be broken for detachment of the parachute 12 by the deposition of mechanical, vibratory, thermal or light energy. The tip of the hollow wire/tube 6 is coated with a chemical to prevent adhesion to the polymer or other material used to fill the parachute 12. Elastic ties 20 adherent to the parachute 12 keep the material of the parachute 12 together after detachment of the parachute 12 from the hollow wire/tube 6. The parachute 12 may be not only mildly elastic, but may also be folded to allow for greater expansion. For example, there may be accordion folds (not shown) or helical folds (not shown) in the parachute to allow it to unwrap and increase in size without significant elasticity of the material of the parachute 12. The parachute may measure up to about 0.5 mm or slightly larger (e.g., to a maximum of 1 mm) in diameter in a non-expanded state. Different sizes of parachutes are available to fill a variety of aneurysms, ranging in size from 8 cubic millimeters to 4 cubic centimeters or more. It is desirable to have the parachute 12 in the non-expanded state as small as possible with it retaining its ability to fill an aneurysm when expanded, so the material must be particularly soft, with newer technology allowing the non-expanded parachute to continue to decrease in size. MR-visible coils 16 are shown around the hollow wire/tube 6 near the opening 10 and similar MR-visible coils 18 are present near the opening 8 of the microcatheter 4. The MR-visible coils 16 and 18 are an improved practice of the invention, with the coils providing responsive signals to magnetic resonance imaging (MRI) so that the device can be viewed by MR imaging in real time while the device is being manipulated and used during an aneurysm occlusion procedure. FIG. 2 shows a parachute 12 attached directly to a microcatheter 4 instead of attachment to a hollow wire/tube. FIG. 3 shows the microcatheter device 2 of FIG. 1, except that there is now an expanded parachute 14 shown with the device 2. Expansion was effected by the passage of a liquid (not shown) through the opening 10 in the hollow wire/tube 6.

Figure 4:
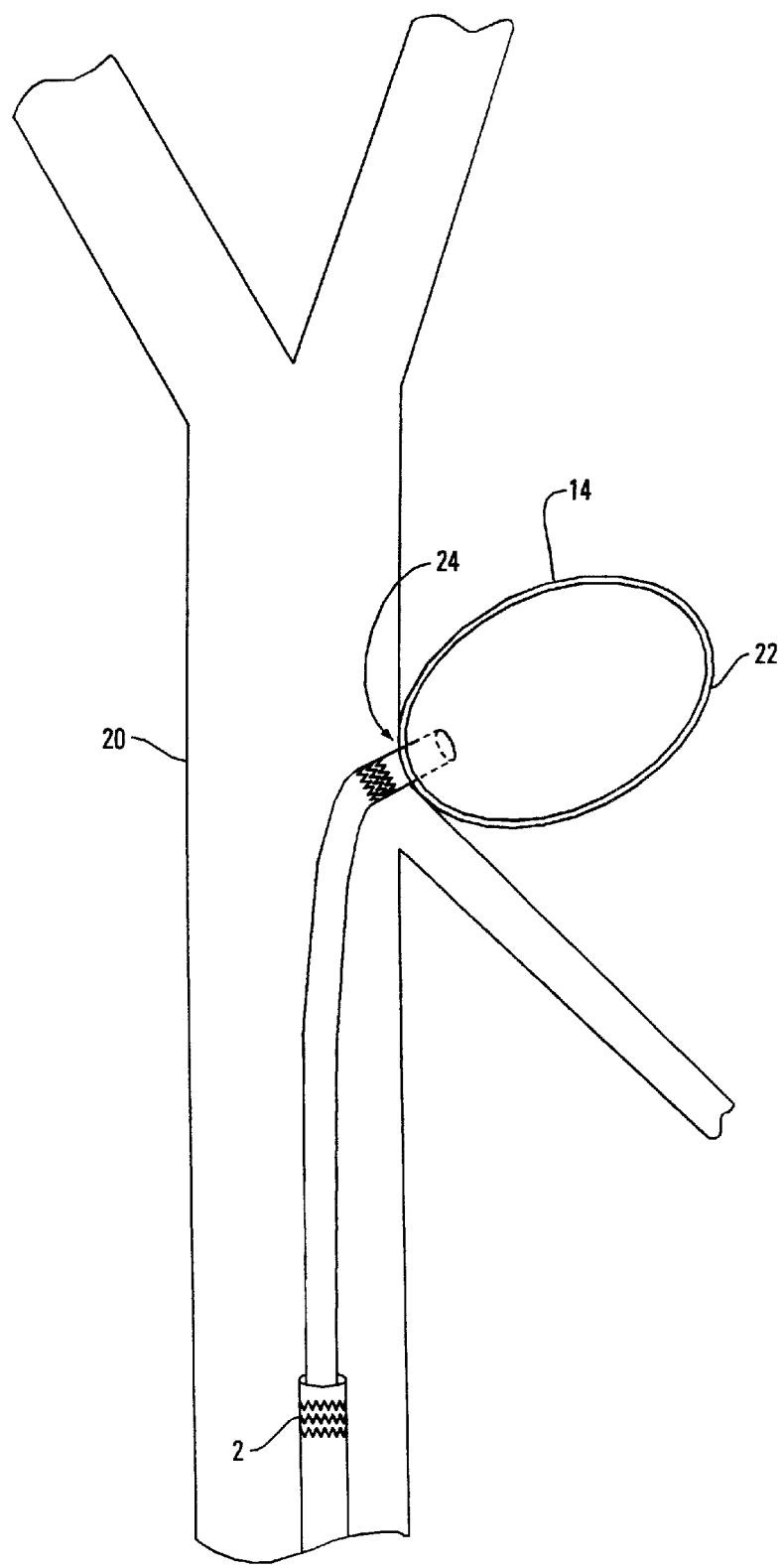
FIG. 4 shows a cerebral blood vessel containing a microcatheter-parachute assembly according to the present invention with a non-expanded parachute inserted into an aneurysm with a narrow neck.
Figure 5:
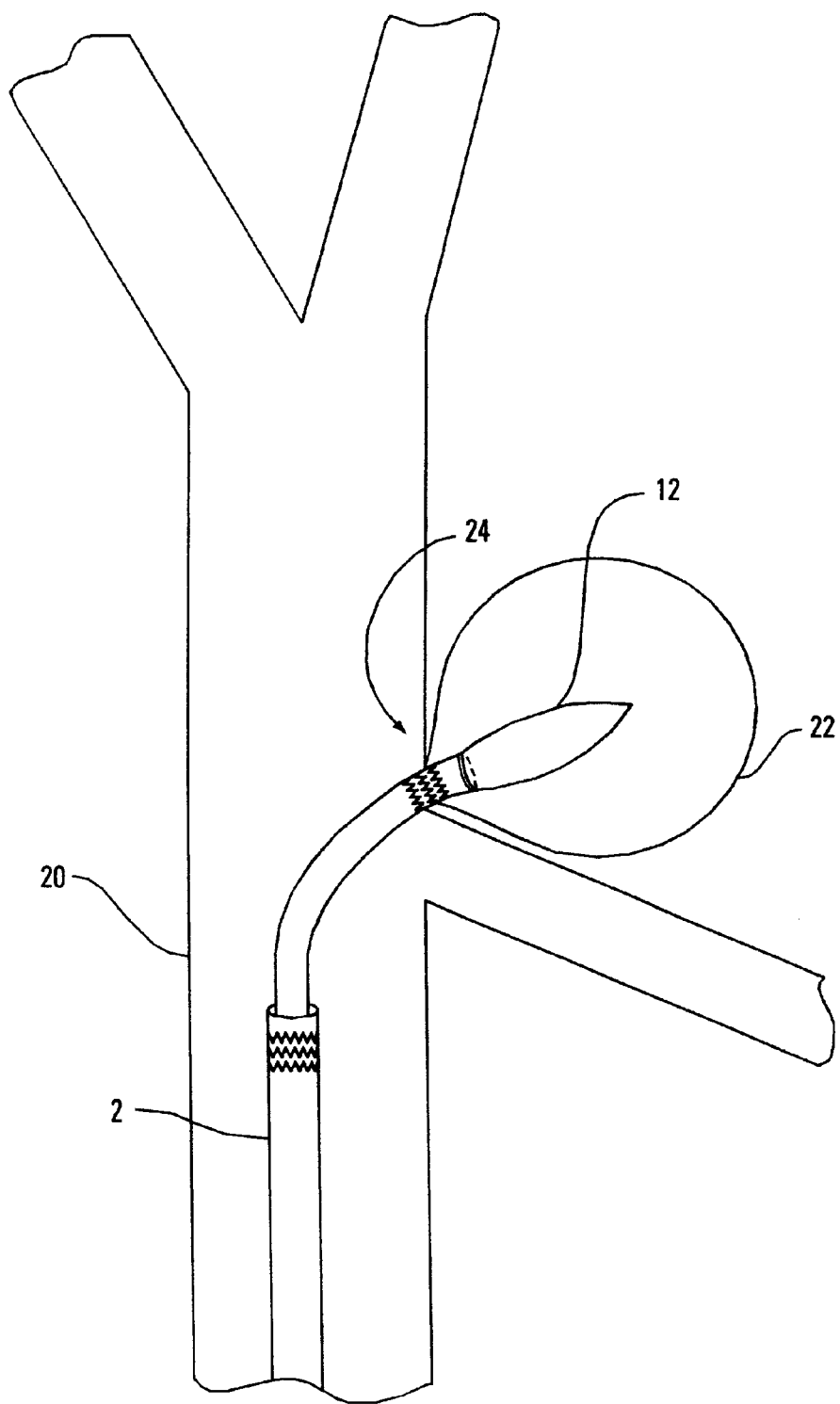
FIG. 5 shows a cerebral blood vessel containing a microcatheter-parachute assembly according to the present invention with an expanded parachute inserted into an aneurysm with a narrow neck.

FIG. 4 shows a microcatheter device 2 according to the invention within a cerebral blood vessel 20 having an aneurysm 22 with a narrow opening (neck) 24 from the blood vessel 20 to the aneurysm 22. The non-expanded parachute 12 is shown within the aneurysm 22. FIG. 5 shows a microcatheter device 2 according to the invention within a cerebral blood vessel 20 having an aneurysm 22 with a narrow opening 24 from the blood vessel 20 to the aneurysm 22. An expanded parachute 14 is shown within the aneurysm 22 abutting or contiguous to, or flush against, the interior surface of the aneurysm 22.

Figure 6:
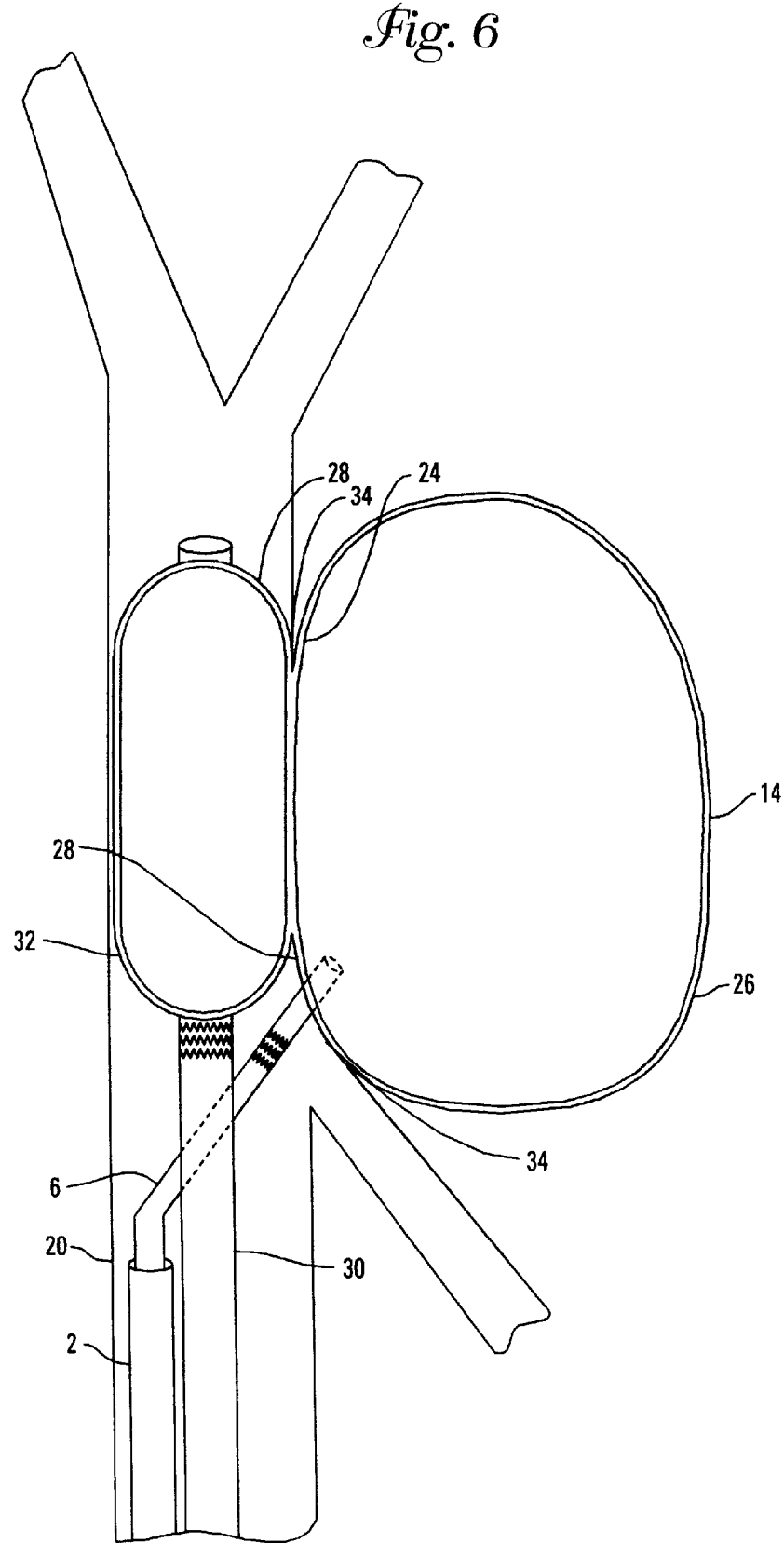
FIG. 6 shows a cerebral blood vessel containing a microcatheter-parachute assembly according to the present invention with an expanded parachute inserted into an aneurysm with a wide neck, using a non-detachable balloon in the blood vessel to help form the parachute contour.

FIG. 6 shows a microcatheter device 2 according to the invention within a cerebral blood vessel 20 having an aneurysm 26 with a wide opening (neck) 28 from the blood vessel 20 to the aneurysm 26. A hollow wire/tube 6 and an expanded parachute 14 are within the aneurysm. There is a second catheter 30 with a non-detachable balloon 32 near its end within the blood vessel 20. There are two lumens within catheter 30, a central one permitting perfusion of fluids such as blood through the catheter into the circulation beyond the catheter when the balloon 32 is expanded, and a second lumen for injection of a liquid to inflate the balloon 32. The inflated balloon 32 covers the majority of the opening 28 of the aneurysm 26, giving a surface against which the parachute 14 may expand. The soft material of the parachute 14 even allows the margins 24 and 34 of the aneurysm to be filled, insuring maximum protection against rupture and aneurysm recurrence. The inflated balloon is placed so that a small portion of the opening 28 of the aneurysm 26 is left uncovered during slow expansion of parachute 14. This allows the egress of blood within the aneurysm during parachute expansion so that there will be no significant change in the pressure within the aneurysm.

The various sizes of inflated parachutes 14 will accept volumes from 0.01 to 4.0 or more cubic centimeters (cc's) of fluid, to fill aneurysms of 2 mm to 4 cm or more in diameter. The parachute is filled through microcatheter 4 or hollow wire/tube 6 with a liquid filler material, preferably a liquid filler material that hardens, and more preferably a liquid filler material that polymerizes such as 2-hydroxyethylmethacrylate or other in situ polymerizing agent, such as cellulose acetate. This minimizes the possibility of contraction of the volume of the parachute. Fluorinated polymeric materials, polyamides and other biologically compatible or inert polymers would be alternative filler materials.

It is of course desirable that all materials used in the device, including the filler material, have minimal adverse biological effects during the procedure and/or when residing within the patient. The materials used for the hollow wire or hollow tube are well known in the art. They may consist of a variety of metals, some of which may be visible with MRI. Alternatively, in order to minimize artifacts if MR is used for guidance during the occlusion procedure, the hollow tube may be made of a plastic material. The polymer materials for the construction of the microcatheter, and the double-lumen balloon catheter if used, are well known in the art. Filler materials for expanding the parachute are also well known in the literature.

Particular attributes and potentialities of the parachute may include a tightly wrapped material to allow significant expansion from a modest size non-expanded parachute. A controlled porosity material may be used for the material of the parachute. For example, the use of a tight weave, Nitinol mesh fabric will allow controlled migration of liquid material across the fabric and enhance migration of connective tissue through the mesh to provide long-term secure adhesion of the parachute to the aneurysm surface. The material of the parachute can comprise, or be coated with, compositions that are visible with MRI or x-ray systems such as fluoroscopy or CT. The parachute material can be coated with or otherwise carry endothelial and fibroblastic growth factors. The size of the parachute can be selected according to the size and the configuration of the aneurysm; a variety of sizes will be available. The parachute should be attached to the hollow tube or hollow wire in such a way that the parachute can be easily separated from the tube or wire. This attachment may be purely physical such as an elastic attachment that is overcome by physically retracting the hollow wire or tube after the polymer within the parachute has hardened sufficiently. An electrical, vibratory, or thermal stimulus may be passed through the hollow wire or tube to reduce the attachment of the parachute to the hollow wire/tube (e.g., by thermally softening or electrically initiating decomposition of an adhesive securing the parachute to the hollow wire/tube). Elastic ties attached to the outer surface of the parachute where it is attached to the hollow wire/tube will contract upon detachment of the parachute and keep the free margins of the parachute closed within the aneurysm. The hollow wire/tube is ordinarily provided with a curved structure so that upon telescoping out of the microcatheter, it can be directed towards or within an aneurysm that is not in direct linear alignment with the long axis of the microcatheter.

The hollow wire/tube, as previously noted, should have an outside diameter that is smaller than the inside diameter of the microcatheter. Ordinarily, the outer diameter for the hollow wire/tube is from 0.2 to 0.75 mm, more preferably from 0.33 to 0.5 mm. The inner diameter is as large as possible while keeping some stiffness to the walls of the wire/tube. The length is from 175 to 195 cm. The microcatheter may be selected from amongst existing microcatheter tubing materials available commercially.

As the parachute element is also preferably passed through a central opening or conductive path through the microcatheter, the parachute should also have dimensions compatible with such a procedure. For example, the parachute element, when associated with a catheter having an inside diameter of about 1.0 mm, the parachute element should have a diameter of less than 1.0 mm when folded. The parachute element preferably has a diameter of less than 0.5 mm when in a fully retracted condition.

In the method of the present invention, MR visibility is achieved by embedding, filling, blending, coating, laminating, placing of MR-emitting/receiving coils or otherwise associating an MR visible material onto sections of the device which are intended to be viewed during MR guidance of the procedure or by MRI after the procedure. The method for passive MR visualization of implantable medical devices disclosed by Ratner (U.S. Pat. Nos. 5,154,179 and 4,989,608) is less preferred because of the potential for image deterioration. The method of Werne (Ser. No. 08/554446, ITI Medical Technologies), which minimizes MR susceptibility artifacts and controls eddy currents in the electromagnetic scattering environment, so that a bright "halo" artifact is created to outline the device in its approximately true size shape, and position, is potentially more useful. In the method of the invention disclosed by ITI, an ultra thin coating of conductive material comprising 1–10% of the theoretical skin depth of the material being imaged—typically about 250,000 angstroms—is applied. By using a coating of 2,000–25,000 angstroms thickness, ITI has found that the susceptibility artifact due to the metal is negligible due to the low material mass. At the same time, the eddy currents are limited due to the ultra-thin conductor coating on the device. Such a technique will allow the parachute to be imaged within the aneurysm by MRI during and after the occlusion procedure, along with the surrounding tissues, with minimal artifact. Active MR visualization of the microcatheter, hollow wire/tube, and balloon catheter (if used) during MR-guidance of the occlusion procedure is provided by MR-visible coils on these devices.

In the method of the present invention, the release mechanism may be effected by overcoming an elastic attachment, or by the application of an electrical, vibratory, thermal or chemical stimulus through the hollow wire/tube. This detachment is preferably achieved by any available mechanical release function. This mechanical release function could, for example, include reduced pressure attachments (e.g., vacuum holders), magnetically held devices, gripped elements (e.g., actuated fingers), electrically activated motivators or the incorporation of a precision manufactured outer sheath made of a metal that is significantly hard and could slide and mechanically release the device. High precision serrations could also be incorporated to essentially saw off or pinch off the point of attachment. The LIGA process can be used to fabricate miniature mechanical components with thickness greater than that which can be achieved with conventional IC processing (>2–5 um). LIGA involves the formation of a plastic mold, such as of polymethyl-methacrylate, by exposure of the material to deep ultraviolet radiation or low energy x-rays. The mold is used in an electroplating process, and then removed. Structures as thick as several hundred microns have been formed in this way with aspect ratios (height to width) well over 50:1. In addition, since the final structural components are electroplated, miniature parts can be made from gold, nickel, copper, or other MR-visible materials. Other means of detachment include electrical, thermal or vibratory stimulation of a point of attachment, or by hydration, change of pH, or change of osmolality of the device/catheter interface.

In the method of the invention, energy deposition in situ could be achieved by the use of lasers and/or optical fibers to deliver energy to the tip of the catheter or hollow wire/tube for the initiation of polymerization, device release, and/or thrombogenesis. Fiber optic transmission within the catheter may also allow for the use of optical reflectometry to provide energy deposition. In the method of the present invention, the ability to administer pharmacologic agents is achieved by surface or lumen-coating technology such as that described in U.S. Pat. No. 5,470,307 to Lindall, which discloses a low-profile catheter system with an exposed coating containing a therapeutic drug agent, which can be selectively released at a remote tissue site by activation of a photosensitive chemical linker. The linker is attached to the substrate via a complementary chemical group, which is configured to accept a complementary bond to the therapeutic drug agent. The drug agent is in turn bonded to a molecular lattice to accommodate a high molecular concentration per unit area and the inclusion of ancillary compounds such as markers or secondary emitters. A preferred method is the device described in U.S. patent application Ser. No. 08/857,043, filed on May 15, 1997 in the names of J. Kucharczyk and M. Moseley. This device allows for the use of multiple lumens and ports in a catheter type delivery device.

When treating a wide-neck (mouth) aneurysm, a double-lumen non-detachable balloon is placed over the mouth of aneurysm to five the parachute a surface against which to expand. The balloons come in various sizes, and measure from 2 to 5 mm in diameter. They are from 0.5 to 3.0 cm in length, inflate within 2 seconds, deflate within 5 seconds, and are attached to catheters of 150 cm in length.

The microcatheter is standard to the industry. It is 150 cm in length, 2.5 French or slightly less outer diameter, 0.53 mm inner diameter, reinforced body, with the distal 15 cm being extremely flexible. A hydrophilic coating is present on the guidewires, on the internal external surfaces of the catheters, and on the outside of the balloon. A coating resistant to the polymer is applied to the end of the hollow wire/tube and to the tip of the microcatheter if the parachute is attached directly to it. This allows detachment of the polymer-filled parachute without the hollow wire/tube or microcatheter being grasped by the polymer.

Preferred Design Criteria for the Microcatheter/Parachute System
  a) deliverable via 2.5 French (Fr) catheter
  b) radiopaque
  c) reflux or leakage of parachute filler back into artery must be avoided
  d) decompression of the blood within the aneurysm while expanding the parachute is necessary to prevent aneurysmal rupture. This is accomplished by slow parachute filling, allowing blood to escape from the aneurysm. Occlusion of wide-neck aneurysms requires a non-detachable balloon over the majority of the mouth of the aneurysm, but a space must be left for the egress of blood during parachute filling. If the pre-occlusion MRI had shown the presence of intraluminal clot, expansion of the parachute would have to be performed with great caution for fear of embolization of that clot to distal vessels.
  e) result must allow for invasion of tissue
  f) delivery device must be able to navigate tortuous vessels
  g) the device must isolate the entire aneurysm from the circulation
  h) the potential for future rupture of the aneurysm must be minimized by completely filling the aneurysm with the polymer-filled parachute
  i) the device must not intrude on the parent vessel; elastic ties will insure that the ends of the parachute do not protrude into the parent vessel. If a wide neck allows the parachute to protrude into the parent vessel, polymerization will have to take place while a non-detachable balloon is in place, and
  j) if temporary occlusion of the parent vessel is required, perfusion of the patient's blood, or a blood substitute, is performed through the central lumen of he double-lumen non-detachable balloon catheter.

Further Description of the Parachute
  a) the combination of polymerization of the filler and the elastic ties to hold the ends of the parachute within the aneurysm may be improved upon by a valve or other stronger sealing mechanism.
  b) some aneurysms have some clot in the distal sack, which must not be allowed to escape from the aneurysm during parachute inflation.

This clot should be recognized and addressed on pre-occlusion MRI.

In accordance with the present invention, in order to have the parachute device expand to a diameter greater than the predetermined diameter, the device is provided with a built-in elastic memory. This built-in elastic memory is achieved by utilizing a plastic such as a polymer that has a molecular transition incorporated in the same. The polymeric material is biocompatible. The polymeric material is composed in such a manner so that the achieved built-in memory can be activated upon subjecting the device to certain factors as hereinafter explained, which may include adsorption of heat by the plastic, adsorption of liquid by the plastic and a change in the pH in the liquid in which the plastic is disposed. In order to make it responsive to the adsorption of a liquid, it is desirable that the polymeric material possesses a range of hydrophilicities ranging from 0 to 50 percent and preferably from 0 to 30 percent. As is understood in the polymer art, polymers may comprise segments of different properties within the polymer chain. The different segments may be provided as a natural result of random polymerization, graft copolymerization, block copolymerization, and other polymeric techniques which combine properties within a polymer or polymer network (as by intermolecular networking polymers). The molecular transitions which can be incorporated in the device can be in the form of thermal transitions, as for example a crystal melting point between $-50°$ C. and $+100°$ C. of the polymer main chain, and a melting point of between $-50°$ C. and $+100°$ C. of a side chain of the polymer capable of crystallizing, a glass transition temperature between $-50°$ C. and $+100°$ C. and a liquid-crystal phase temperature transition between $-50°$ C. and $+100°$ C. The molecular transitions can also include a local mode molecular transition also accessed by heat.

In accordance with the present invention, various formulations can be utilized for preparing a polymeric material that can be utilized for achieving built-in elastic memories in the device of the present invention. The types of formulations that can be used are set forth in the examples below.

Once the parachute device has been positioned in the lumen of the aneurysm, heat can be applied in order to cause the parachute device to assume the greater diameter in its memory. Thermal activation of the memory of the device can be achieved by introducing a gas or liquid, preferably a liquid because of its greater heat transfer capabilities, to the microcatheter lumen in the flexible element 6 and introducing the same into the parachute 12 to inflate the parachute 14. The heated liquid in the parachute will cause heat to be rapidly transferred to the parachute device to raise the temperature of the device until the temperature reaches the glass transition temperature allowing the parachute to return to its recovery diameter. This recovery is facilitated by the expansion of the parachute 14 that applies outwardly extending forces to the internal diameter of the aneurysm. It should be appreciated that to stop the flow of a liquid, such as blood, through a passage, it is merely necessary that the liquid be removed from the parachute 14 and the parachute 14 be deflated, and thereafter again reinflated until the parachute device Las expanded to firmly engage the walls of the aneurysm so that it will be frictionally retained therein.

In the method of the invention, the recovery diameter in the memory of the aneurysm occlusion device can also be achieved by permitting the parachute to adsorb water from a body fluid, as for example, from the blood in an aneurysm. The device can also assume its recovery diameter by being subjected to the pH level of the liquid in which the device is disposed. According to the method of the invention, the return to the recovery diameter can also be aided by outward pressures of a liquid or other material within the parachute. Alternatively, infrared, microwave or radiofrequency sources as well as resistive heating can be utilized for supplying such external heat to the parachute.

In order to enhance ingrowth of intima and endothelial vessel tissue into the aneurysm, the parachute device can be made of a porous material to enhance compatibility of the device with the vessel. Examples of stents made of such materials are set forth in patents cited above relating to stents.

The porosity of the wall of the device again permits the ingrowth of intimal endothelial tissue to enhance compatibility of the device with the vessel. Thus it can be seen that device of the present invention can be formed so as to enhance the ingrowth of intimal endothelial tissue which helps to ensure that the device will remain in the desired location within the aneurysm and will not move about in the vessel. Such endothelial vessel tissue growth should occur within approximately four weeks after insertion into the aneurysm.

In addition, devices of the present invention can be formulated so as to be able to carry a drug agent, such as thrombolytic agents, growth factors and slow-release medications. Also, controlled release drug administration can be provided by utilizing the material of the device as an inert polymeric drug carrier. For example, the drug may be incorporated in a controlled release system as a dispersion in a matrix. The matrix can be formed with a dispersion of uniform drug particles in the biocompatible polymeric materials of the type hereinbefore described in connection with the device of the present invention.

From the foregoing it can be seen that there has been provided an aneurysm occlusion device incorporating the present invention and an apparatus and method for use therewith which has numerous advantages. The device has low protein absorption and is thus biocompatible. The device can be provided with a desired hydrophilicity to improve its compatibility with the vessel. The device can be made with a desired stiffness so as to match the compliance of the vessel. Because of its built-in memory, the device need not be physically constrained prior to use to prevent premature recovery. The device can be made porous to facilitate the ingrowth of intimal and endothelial cells. The device can be formulated and/or treated so as to carry medical agents that remain with the stent.

In general, the polymer compositions can be containing one or more of the following: acrylic acid, methacrylic acid, esters of acrylic acid and methacrylic acid and combinations thereof. Such compositions can also be provided which contain acrylic acid, methacrylic acid, esters of acrylic acid and methacrylic acid with N-vinyl pyrrolidone. Compositions can also be provided containing copolymers of ethylene oxide and vinyl monomers and other compositions that contain acrylamide esters. Other compositions can contain acrylic acid, methacrylic acid, acrylic esters, methacrylic esters, vinyl pyrrolidone and acrylamide esters. These compositions can contain copolymers of vinyl pyrrolidone and monomers and alternatively copolymers of maleic anhydride. Compositions also can be provided containing blends of polymers such as polyethylene oxide, polyoctenylene, polyethylene, polysiloxanes, nylons and polyesters. Other compositions can contain polymers and plasticizers.

Actual processes of the invention may be practiced as follows: For a narrow-neck aneurysm, the aneurysm is first catheterized by standard techniques using microcatheters and standard microguidewire systems. The standard microguidewire is then removed, and the parachute device attached to the hollow wire or hollow tube is guided into the aneurysm. The parachute is tightly wrapped into an unexpanded position. The parachute is slowly expanded within the aneurysm, e.g., by using a filler solution (as described herein, with polymerizing fluids, if needed) or by first providing a saline solution through the hollow wire. The expanding solution, if it is a saline solution, is then displaced by a filler composition, preferably a radiopaque filler composition that polymerizes over time. The infusion will be controlled by amounts determined or predetermined necessary to fill the volume of the aneurysm. A test is performed (e.g., by angiogram) to assure complete aneurysm occlusion. The parachute is then released from the hollow wire and the hollow wire/tube and microcatheter are removed.

In the process of treating a wide-neck aneurysm, the process is essentially identical through the step of expanding the parachute within the aneurysm. In this case, however, an alternative procedure is available of providing a non-detachable balloon catheter (NDBC) across the mouth of the aneurysm and inflating the balloon. The patient's blood or its equivalent is infused through the NDBC. The filler (e.g., polymer) is infused into the parachute, and then the process is continued as with the narrow-neck aneurysm where the infusion of the parachute filler (e.g., plus polymerizable material, if needed) is effected.

Alternative Methods of Practicing the Art of the Invention (1) The aneurysm may be filled with a mechanically detachable compliant radiopaque and MR visible hydrogel occlusion device. The device should have a helix-like configuration to maximize surface area for thrombogenesis; should be very soft and compliant; available in a variety of sizes, lengths and shapes; easily deliverable through catheters with internal diameters of 0.025–0.053 cm; radioopaque to x-rays and MR-visible; thrombogenic; contain chemical agents to stimulate thrombus formation, and the ingrowth of collagen and endothelium; and, should easily conform to the aneurysm lumen without exerting high lateral stresses which might cause rupture. In the case of an hydrogel device, the presumed mechanism of detachment activation is hydration of the hydrogel/catheter interface. However, detachment activation could also be effected by thermal exchange coupling or transduction, or by pH or osmolality changes. Between 4–8 coils might be needed per aneurysm treated, depending upon the size of the aneurysm and the sizes of hydrogel coils selected.

(2) Hydrogel-based particulate emboli, 150–1000 micron in diameter, with a hollow core which contains porous hydrogels or degradable polymers with slow release macromolecules which act as biologic modifiers. The macromolecules would ideally be MRI visible and act as antithrombolysis agents to prevent recanalization of the aneurysm lumen. Peptide molecules could also be used to induce fibroblast and/or endothelial growth. Pre-clinical thrombogenicity tests would evaluate the adsorption of proteins, response of blood cells, and activation of blood clotting mechanisms.

(3) The aneurysm occlusion device could be constructed of cylindrical components formed of a plastic material. The device would have a predetermined diameter and memory of first- second- and third-order diameters. The memory plastic would assume the greater diameter in its memory upon occurrence of one or more of the following conditions:

(a) adsorption of heat by the plastic;

(b) adsorption of liquid by the plastic; and (c) a change in pH in the liquid in contact with the plastic.

In the delivery apparatus and method of the invention, a microcatheter is utilized for delivering the parachute device to the desired cerebrovascular location. A balloon attached to a smaller microcatheter, both within the larger microcatheter, may help to inflate the parachute. When the balloon and the parachute device thereon has been delivered to the desired site, the balloon can be inflated to help expand the parachute when the parachute is subjected to certain factors and conditions. Thereafter the balloon is deflated and the balloon catheter is removed leaving the parachute device in place. The device is caused to assume the greater diameter of its memory by the adsorption of heat by the plastic, the adsorption of liquid by the plastic, or a change in the pH in the liquid surrounding the plastic.

(4) The parachute device may be in the form of a generally cylindrical tubular member made of polymeric resin or composite material. The member is provided with a cylindrical wall that forms a flow passage or lumen extending therethrough. The ends of the member are closed to provide chambers. It should be appreciated that although the cylindrical wall has been described as continuous, it can be discontinuous as desired. For example, the wall can be in the form of a helix in which the device in the form of a cylindrical member formed by turns or loops, as with a spring, with a lumen extending therethrough and with chambers or end portions provided. It should be appreciated that other constructions can be utilized, as for example one having a perforated wall with openings or holes of various sizes therein.

The member may be formed of a plastic material and has a predetermined diameter. The material is of a type that has a built-in elastic memory of a diameter greater than the predetermined diameter. The size, diameter and length of the device is tailored to the aneurysm for which the device is to be utilized. For example, for aneurysms 0.5 to 10.0 mm in diameter, the device can have an unextended length ranging from about 0.3 or 0.4 mm to about 8 or 9 mm. (with the extended length being from 1.4 to 10 times, preferably from about 1.5 to 4 or 5 times the unextended length). The member can have a diameter ranging, for example, from about 0.02 or 0.05 or 0.1 mm. to about 8.0 or 9.0 mm. with a wall thickness ranging from about 2 to about 500 or 1000 microns. To facilitate its introduction into a vessel, the diameter of the device is reduced by a suitable amount, as for example 10 to 30 percent. However, it should be appreciated that, if desired, the reduction can be sufficiently great so that when the device returns to its original expanded state it could have expanded by 400 to 500 percent (or more) from its predetermined diameter.

(5) The device of the present invention can be inflated by a balloon inserted into the parachute device. For example, the delivery site can be an arterial vessel in the neck that is provided with a flow passage therein. A guiding catheter of a conventional type can be introduced into the patient through the femoral artery and advanced into a position adjacent to the site of the aneurysm. In the method of the invention a variety of balloon catheters of a conventional type can be utilized. As is well known to those skilled in the art, the balloon catheter is provided with a flexible elongated element which has a balloon inflation lumen disposed therein which is in communication with a balloon mounted on the distal extremity of the flexible elongated element. The balloon catheter is also provided with a guidewire that can be of a fixed type or a movable guidewire of types well known to those skilled in the art. With the balloon catheter outside of the patient's body, the balloon is deflated and a parachute aneurysm occlusion device of the type hereinbefore described is slid over the deflated balloon so that it is frictionally engaged by the balloon. The balloon catheter with the parachute device thereon (including attachment to a microcatheter) is then introduced into the guiding catheter that has already been positioned in the patient's body for the endovascular procedure. The balloon catheter is advanced in the conventional manner so that it is advanced into the aneurysm lumen. Radiopaque elements typically are carried by the balloon catheter in the vicinity of the balloon to facilitate locating the lumen of the balloon catheter as it is advanced in the vessel of the patient. The balloon with the device is moved into the arterial passage so that it is lodged within the aneurysm lumen. The balloon is inflated in order to expand the parachute device. The balloon is not inflated to the full size of the aneurysm. The balloon and its attached catheter are then removed from the microcatheter containing the parachute, and the parachute is filled with a liquid material (e.g., the liquid hardenable material such as the liquid hardenable or polymerizable material) that will harden over a relatively short period of time (within a few minutes, preferably less than one minute, and most preferably in less than 30 seconds). The parachute device is then detached from the hollow tube/wire or microcatheter and left within the aneurysm.

Thus, since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the broadest interpretation of the appended claims, rather than being limited to the embodiments shown and discussed in the foregoing description, and all changes which come within the meaning and range of equivalency of the claims are intended to be embraced therein.

What is claimed is:

1. An image guidance system for the treatment or thrombotic occlusion of aneurysms in the human cerebrovascular system under either x-ray fluoroscopy or magnetic resonance imaging guidance, said system comprising:

(a) a magnetic resonance-visible or X-ray visible aneurysm occlusion instrument, wherein said instrument comprises i) a at least one elongate element selected from the group consisting of a guidewire and a microcatheter, ii) a hollow wire or hollow tube, and iii) an expansile parachute device temporarily attached to an open end of said hollow wire or hollow tube;

(b) at least one imaging system selected from the group consisting of x-ray fluoroscopy or magnetic resonance imaging which is capable of detecting the position and orientation of said aneurysm occlusion instrument within the human cerebrovascular system;

(c) an image display means for acquiring a medically diagnostic image of a region of interest from said at least one imaging system selected from the group consisting of x-ray fluoroscopy or magnetic resonance imaging; and (d) a source of hardenable liquid.

2. The system of claim 1 wherein said expansile parachute device comprises a magnetic resonance imaging-visible parachute device having a plurality of elongated filamentary loops made of an expansile material.

3. The system of claim 1 wherein at least some surfaces of the instrument are impregnated with a magnetic resonance-visible material which enables continuous magnetic resonance visualization of the instrument when viewed with magnetic resonance imaging systems.

4. The system of claim 1 wherein said magnetic resonance-visible aneurysm occlusion instrument consists of at least one component selected from the group consisting of i) hydrogel or polymer coil, ii) stent components, and (iii) memory metals.

5. The system of claim 1 wherein said magnetic resonance-visible aneurysm occlusion instrument has a helix-like configuration.

6. The system of claim 1 wherein said magnetic resonance-visible aneurysm occlusion instrument is impregnated with a magnetic resonance-visible contrast material.

7. The system of claim 1 wherein the aneurysm occlusion instrument comprises a memory metal or polymeric material having an initial built-in elastic predetermined diameter, which is less than the diameter of a lumen in a blood vessel within the brain of a human, so that the instrument can be inserted into the lumen of said vessel, said memory metal or polymeric material also being characterized in that it will assume a greater diameter and move into engagement with the wall of the vessel upon activation of a property of said polymeric material which causes the polymeric material to expand.

8. The system of claim 1 wherein said expansile parachute device is detachably connected to said microcatheter or guidewire and detachment of the expansile parachute device from said microcatheter or guidewire can be achieved by at least one process selected from the group consisting of mechanical decoupling, hydration of the instrument/microcatheter interface, thermal exchange coupling, transduction, memory change, pH change, or osmolality change.

9. The system of claim 8 wherein detachment occlusion instrument can be achieved by attaining one or more of:
  (a) a thermal softening of a physical adherent between said instrument and said catheter or guidewire;
  (b) a melting point of the a portion of the polymer chain;
  (c) a glass transition temperature; and
  (d) a crystal phase transition.

10. A process for the treatment of aneurysms in the human cerebrovascular system under magnetic resonance imaging or X-ray fluoroscopy, said process comprising the steps of:
  (a) determining the volume of an aneurysm in the cerebrovascular system and selecting a parachute system of a size and configuration appropriate to the volume of the aneurysm;
  (b) catheterizing the aneurysm with a microcatheter;
  (c) removing the microcatheter and replacing it with a hollow device having an attached parachute system selected in accordance with step a);
  (d) injecting a liquid to partially enlarge or expand the parachute;
  (e) injecting a hardenable liquid to fill the parachute within the confines of the aneurysm;
  (f) verify isolation of the aneurysm from its parent blood vessel with imaging techniques selected from the group consisting of magnetic resonance imaging or X-ray fluoroscopy;
  (g) detach the parachute from the hollow device, leaving the parachute in the aneurysm; and
  (h) remove the hollow device.

11. The process of claim 10 wherein said hollow device with attached parachute comprises:
  (a) an MR-visible aneurysm occlusion instrument, wherein said instrument comprises a guidewire, a catheter, a balloon, and an expansive parachute device; and performing a beneficial procedure upon said thrombotic occlusion in the cerebrovascular system with said device.

12. The process of claim 11 wherein said beneficial procedure comprises inflating a balloon and having a surface of said balloon positioned against an interior surface of the parachute within the aneurysm.

13. The process of claim 11 for treating intracranial and extracranial circulatory regions wherein instruments used in the process
  wherein the parachute system is selected such that the parachute has a fluid conductive opening to said microcatheter.

14. The process of claim 13 wherein said microcatheter and said parachute are of dimensions small enough to pass through a central opening in a catheter.

15. The process of claim 14 wherein said catheter has an inside diameter of less than 2 millimeters and said microcatheter has an outside diameter of from 0.2 to 0.75 mm.

16. The process of claim 15 wherein said parachute has a diameter of less then 1.0 mm when in a fully retracted condition.

17. The process of claim 15 wherein said parachute has a diameter of less then 0.50 mm when in a fully retracted condition.

18. The process of claim 17 wherein said parachute has a diameter of greater than 2 mm and less than 5 cm when fully extended.

19. A process for treatment of a wide-neck aneurysm with imaging to monitor progress of delivery of a microcatheter device to a site of an aneurysm by x-ray fluoroscopy or magnetic resonance imaging, the process comprising:
  inserting a microcatheter with a parachute attachment into an aneurysm having an opening into a parent vessel,
  inserting a hollow catheter with a balloon element into the parent vessel while imaging the site of the aneurysm by x-ray fluoroscopy or magnetic resonance imaging,
  inflating the balloon to at least partially occlude the opening to the aneurysm,
  deploying the parachute attachment from the microcatheter by the injection of a hardenable liquid into the parachute, and
  after the parachute has been deployed against interior surfaces of the aneurysm, detaching the parachute from the microcatheter; and
  detaching the balloon and removing it from a parent vessel for the aneurysm.

20. The process of claim 19 wherein after the hardenable material has at least partially hardened, the balloon is deflated and the hollow catheter removed, and the parachute detached from the microcatheter and left in place to occlude the aneurysm.

21. The process of claim 19 wherein high-speed magnetic resonance imaging is the imaging used to monitor progress of delivery of the device to a site of an aneurysm.

22. The process of claim 19 wherein high-speed magnetic resonance imaging is used to assist in real time repositioning or removal of at least a portion of said device.

23. The process of claim 19 in which said process is used to treat hemodynamically significant aneurysms by inducing thrombus formation, collagen formation, fibroblast growth and endothelial ingrowth within the aneurysm by delivery of biologic modifier drugs.

24. The process of claim 19 in which said process is used to treat intracranial aneurysms.

25. The process of claim 24 wherein said intracranial aneurysms are selected from the group consisting of aneurysms of the basilar, middle cerebral, anterior cerebral and posterior cerebral arteries.

26. The process of claim 19 wherein said process also includes at least one step comprised of administering local pharmacologic therapies.

* * * * *